(12) United States Patent
Sato et al.

(10) Patent No.: US 6,455,584 B1
(45) Date of Patent: Sep. 24, 2002

(54) PROSTAGLANDIN E₁ DERIVATIVES

(75) Inventors: Fumie Sato, 2-1-901, Kugenumahigashi, Fujisawa-shi, Kanagawa 251-0026 (JP); Tohru Tanami, Tokyo (JP); Hideo Tanaka, Tokyo (JP); Naoya Ono, Tokyo (JP); Makoto Yagi, Tokyo (JP); Hitomi Hirano, Tokyo (JP)

(73) Assignees: Taisho Pharmaceutical Co., Ltd. (JP); Fumie Sato (JP)

( * ) Notice: Subject to any disclaimer, the term of this patent is extended or adjusted under 35 U.S.C. 154(b) by 0 days.

(21) Appl. No.: 09/937,782

(22) PCT Filed: Apr. 7, 2000

(86) PCT No.: PCT/JP00/02286

§ 371 (c)(1), (2), (4) Date: Jan. 4, 2002

(87) PCT Pub. No.: WO00/61550

PCT Pub. Date: Oct. 19, 2000

(30) Foreign Application Priority Data

Apr. 9, 1999 (JP) ............................................ 11-103323

(51) Int. Cl.⁷ .............................................. C07C 177/00
(52) U.S. Cl. ...................... 514/530; 514/573; 560/121; 182/503
(58) Field of Search ........................ 560/121; 562/503; 514/530, 573

(56) References Cited

U.S. PATENT DOCUMENTS

| | | |
|---|---|---|
| 4,029,681 A | 6/1977 | Smith |
| 4,131,738 A | 12/1978 | Smith |
| 5,516,796 A | 5/1996 | Stjernschantz et al. |

FOREIGN PATENT DOCUMENTS

| | | |
|---|---|---|
| JP | 52-100446 | 8/1977 |
| JP | 1-502117 | 7/1989 |
| JP | 10-175948 | 6/1998 |
| WO | 95/25520 | 3/1995 |

*Primary Examiner*—Paul J. Killos
(74) *Attorney, Agent, or Firm*—Lorusso & Loud

(57) ABSTRACT

To provide a prostaglandin derivative represented by the formula:

wherein A is an ethylene group, a vinylene group, an ethynylene group, $O(CH_2)_q$ or $S(O)_r(CH_2)_q$, $R^1$ is a $C_{3-10}$ cycloalkyl group, a $C_{1-4}$ alkyl-$C_{3-10}$ cycloalkyl group, a $C_{3-10}$ cycloalkyl-$C_{1-4}$ alkyl group, a $C_{1-10}$ alkyl group, a $C_{1-10}$ alkyl group substituted with hydroxyl group(s) or $C_{1-4}$ alkoxy group(s), a $C_{2-10}$ alkenyl group, a $C_{2-10}$ alkenyl group substituted with hydroxyl group(s) or $C_{1-4}$ alkoxy group(s), a $C_{2-10}$ alkynyl group, a $C_{2-10}$ alkynyl group substituted with hydroxyl group(s) or $C_{1-4}$ alkoxy group(s) or a bridged cyclic hydrocarbon group, $R^2$ is a hydrogen atom, a $C_{1-10}$ alkyl group or a $C_{3-10}$ cycloalkyl group, m is an integer of 1 to 5, n is an integer of 1 to 4, p is 0, 1 or 2, q is an integer of 1 to 5 and r is 0, 1 or 2; a pharmaceutically acceptable salt thereof or a hydrate thereof exhibit excellent action in inhibiting the growth of vascular smooth muscle and is useful as a drug for inhibition of restenosis after percutaneous transluminal coronary angioplasty.

7 Claims, No Drawings

PROSTAGLANDIN E₁ DERIVATIVES

TECHNICAL FIELD

The present invention relates to novel prostaglandin derivatives, pharmaceutically acceptable salts thereof and hydrates thereof.

BACKGROUND ART

Since prostaglandin (hereinafter referred to as "PG") exhibits various important physiological actions in a trace amount, the syntheses of a large number of derivatives from natural PGs and the biological activities have been investigated with the intention of a practical use as medicines and have been reported in many literatures, for example, Japanese Patent Kokai No. 52-100446 and U.S. Pat. No. 4,131,738.

PG and the derivatives thereof have biological actions such as a vasodilating action, a prophlogistic action, an inhibitory action of blood platelet aggregation, a uterine muscle contraction action, an intestine contraction action or a lowering action of intraocular pressure, and are useful for therapy or prevention of myocardial infarction, angina pectoris, arteriosclerosis, hypertension, labor induction, etc.

On the other hand, percutaneous transluminal coronary angioplasty (PTCA) has low invasiveness to the patient as a therapeutic modality of ischemic heart diseases and has an excellent initial therapy effect, therefore, it is a plasty which recently has rapidly been developed. However, there has been an unsolved drawback of causing restenosis of coronary artery at a frequency of 30–40% within a few months after PTCA.

The compounds which can control not only the migration from intima to mesothelium of vascular smooth muscle cells deeply associating with the onset of restenosis but also their growth in the mesothelium are greatly expected to be usable as drugs for prevention of the restenosis caused after PTCA. However, no clinically available drugs have been found.

An object of the present invention is to provide novel PG derivatives which exhibit excellent action in inhibiting the growth of vascular smooth muscle and are useful as a drug for prevention of restenosis after PTCA.

DISCLOSURE OF THE INVENTION

As a result of the continued extensive studies, the present inventors have found that the prostaglandin derivatives having a triple bond between the 13- and 14-positions and a hydroxyalkylthio group at the 11-position attain the above-mentioned object, and thereby the present invention has been accomplished.

That is, the present invention is directed to a prostaglandin derivative represented by the following Formula (I):

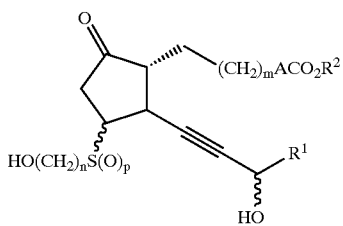

wherein A is an ethylene group, a vinylene group, an ethynylene group, $O(CH_2)_q$ or $S(O)_r(CH_2)_q$, $R^1$ is a $C_{3-10}$ cycloalkyl group, a $C_{1-4}$ alkyl-$C_{3-10}$ cycloalkyl group, a $C_{3-10}$ cycloalkyl-$C_{1-4}$ alkyl group, a $C_{1-10}$ alkyl group, a $C_{1-10}$ alkyl group substituted with hydroxyl group(s) or $C_{1-4}$ alkoxy group(s), a $C_{2-10}$ alkenyl group, a $C_{2-10}$ alkenyl group substituted with hydroxyl group(s) or $C_{1-4}$ alkoxy group(s), a $C_{2-10}$ alkynyl group, a $C_{2-10}$ alkynyl group substituted with hydroxyl group(s) or $C_{1-4}$ alkoxy group(s) or a bridged cyclic hydrocarbon group, $R^2$ is a hydrogen atom, a $C_{1-10}$ alkyl group or a $C_{3-10}$ cycloalkyl group, m is an integer of 1 to 5, n is an integer of 1 to 4, p is 0, 1 or 2, q is an integer of 1 to 5 and r is 0, 1 or 2; a pharmaceutically acceptable salt thereof or a hydrate thereof.

Preferred compounds of the present invention are those of Formula (I) wherein $R^1$ is a $C_{5-10}$ alkyl group, a $C_{5-10}$ alkyl group substituted with hydroxyl group(s) or $C_{1-4}$ alkoxy group(s), a $C_{5-10}$ alkenyl group, a $C_{5-10}$ alkenyl group substituted with hydroxyl group(s) or $C_{1-4}$ alkoxy group(s), a $C_{5-10}$ alkynyl group, or a $C_{5-10}$ alkynyl group substituted with hydroxyl group(s) or $C_{1-4}$ alkoxy group(s), and q is 1 or 2, and specially preferred compounds are those of Formula (I) wherein m is an integer of 2 to 4, and n is 2 or 3.

Furthermore, the present invention is directed to a pharmaceutical preparation which comprises as an effective ingredient a compound represented by Formula (I), a pharmaceutically acceptable salt thereof or a hydrate thereof.

The terms used in the present invention are defined as follows:

The vinylene group refers to a cis- or trans-vinylene group.

The $C_{3-10}$ cycloalkyl group means a cycloalkyl group having 3 to 10 carbon atoms, and examples thereof are a cyclopropyl group, a cyclobutyl group, a cyclopentyl group, a cyclohexyl group and a cycloheptyl group.

The $C_{1-4}$ alkyl-$C_{3-10}$ cycloalkyl group means a cycloalkyl group having 3 to 10 carbon atoms substituted with a straight or branched alkyl group having 1 to 4 carbon atoms, and examples thereof are a methylcyclopropyl group, a methylcyclohexyl group and an ethylcyclohexyl group.

The $C_{3-10}$ cycloalkyl-$C_{1-4}$ alkyl group means a straight or branched alkyl group having 1 to 4 carbon atoms substituted with a cycloalkyl group having 3 to 10 carbon atoms, and examples thereof are a cyclopropylmethyl group, cyclobutylmethyl group, a cyclopentylmethyl group, a cyclopentylethyl group, a cyclohexylmethyl group, a cyclohexylethyl group and a cycloheptylmethyl group.

The $C_{1-10}$ alkyl group means a straight or branched alkyl group having 1 to 10 carbon atoms, and examples thereof are a methyl group, an ethyl group, a propyl group, a butyl group, an isobutyl group, a tert-butyl group, a pentyl group, an isopropyl group, a hexyl group, a heptyl group, an octyl group, a 1-methylpentyl group, a 2-methylpentyl group, a 1-methylhexyl group, a 2-methylhexyl group, a 2,4-dimethylpentyl group, a 2-ethylpentyl group, a 2-methylheptyl group, a 2-ethylhexyl group, a 2-propylpentyl group, a 2-propylhexyl group, a 2,6-dimethylheptyl group, a nonyl group and a decyl group.

The $C_{1-10}$ alkyl group substituted with hydroxyl group(s) or $C_{1-4}$ alkoxy group(s) means a straight or branched alkyl group having 1 to 10 carbon atoms substituted with hydroxyl group(s) or straight or branched alkoxy group(s) having 1 to 4 carbon atoms, and examples thereof are a 5-hydroxy-2-methylpentyl group, a 4,5-dihydroxypentyl group, a 5-methoxy-2-methylpentyl group, a 4-ethoxybutyl group or a 4-allyloxybutyl group.

The $C_{2-10}$ alkenyl group means a straight or branched alkenyl group having 2 to 10 carbon atoms, and examples thereof are a vinyl group, an allyl group, a 2-propenyl group, a 3-pentenyl group, a 4-hexenyl group, a 5-heptenyl group, a 4-methyl-3-pentenyl group, a 2,4-dimethyl-3-pentenyl group, a 6-methyl-5-heptenyl group and a 2,6-dimethyl-5-heptenyl group.

The $C_{2-10}$ alkenyl group substituted with hydroxyl group (s) or $C_{1-4}$ alkoxy group(s) means a straight or branched alkenyl group having 2 to 10 carbon atoms substituted with hydroxyl group(s) or straight or branched alkoxy group(s) having 1 to 4 carbon atoms, and examples thereof are a 6-hydroxy-2-methyl-3-hexenyl group and a 6-methoxy-3-hexenyl group.

The $C_{2-10}$ alkynyl group means a straight or branched alkynyl group having 2 to 10 carbon atoms, and examples thereof are an ethynyl group, a 2-propynyl group, a 3-pentynyl group, a 3-hexynyl group, a 4-hexynyl group, a 1-methylpent-3-ynyl group, a 2-methylpent-3-ynyl group, a 1-methylhex-3-ynyl group and a 2-methylhex-3-ynyl group.

The $C_{2-10}$ alkynyl group substituted with hydroxyl group (s) or $C_{1-4}$ alkoxy group(s) means a straight or branched alkynyl group having 2 to 10 carbon atoms substituted with hydroxyl group(s) or straight or branched alkoxy group(s) having 1 to 4 carbon atoms, and examples thereof are a 5-hydroxy-1-methylpent-3-ynyl group and a 6-methoxy-3-hexynyl group.

Examples of the bridged cyclic hydrocarbon group are a bornyl group, a norbornyl group, an adamantyl group, a pinanyl group, a thujyl group, caryl group and a camphanyl group.

Examples of the pharmaceutically acceptable salt are salts with alkali metal (e.g. sodium or potassium), alkali earth metal (e.g. calcium or magnesium), ammonia, methylamine, dimethylamine, cyclopentylamine, benzylamine, piperidine, monoethanolamine, diethanolamine, monomethyl-monoethanolamine, tromethamine, lysine, a tetraalkyl ammonium and tris(hydroxymethyl)aminomethane.

The compounds of Formula (I) can be prepared, for example, by the methods summarized by the following reaction scheme (wherein, $A^1$ is an ethylene group, a vinylene group, an ethynylene group, $O(CH_2)_q$ or $S(CH_2)_q$, $A^2$ is an ethylene group, a vinylene group, an ethynylene group, $O(CH_2)_q$ or $S(O)_{r1}(CH_2)_q$, $R^3$ is $R^2$ other than a hydrogen atom, p1 is 1 or 2, r1 is 1 or 2, and $R^1$, m, n and q are as defined above).

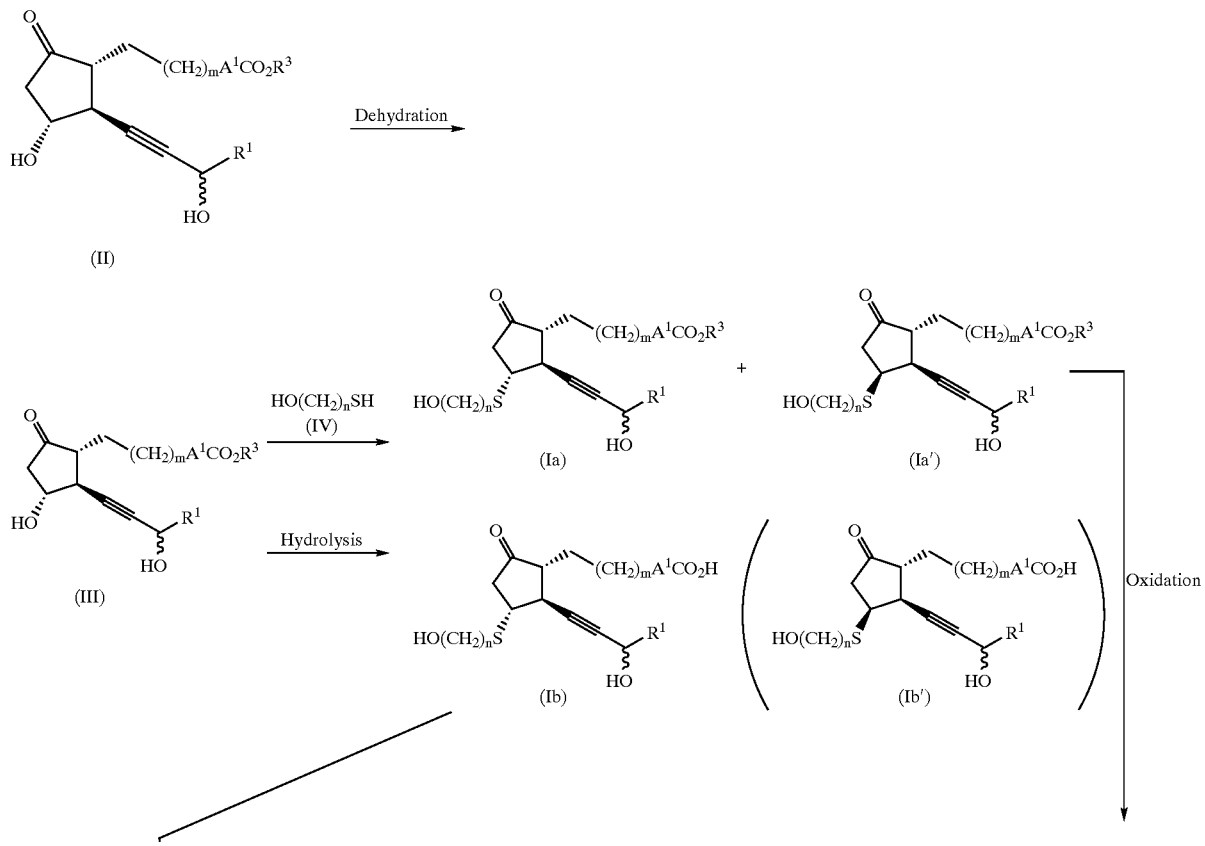

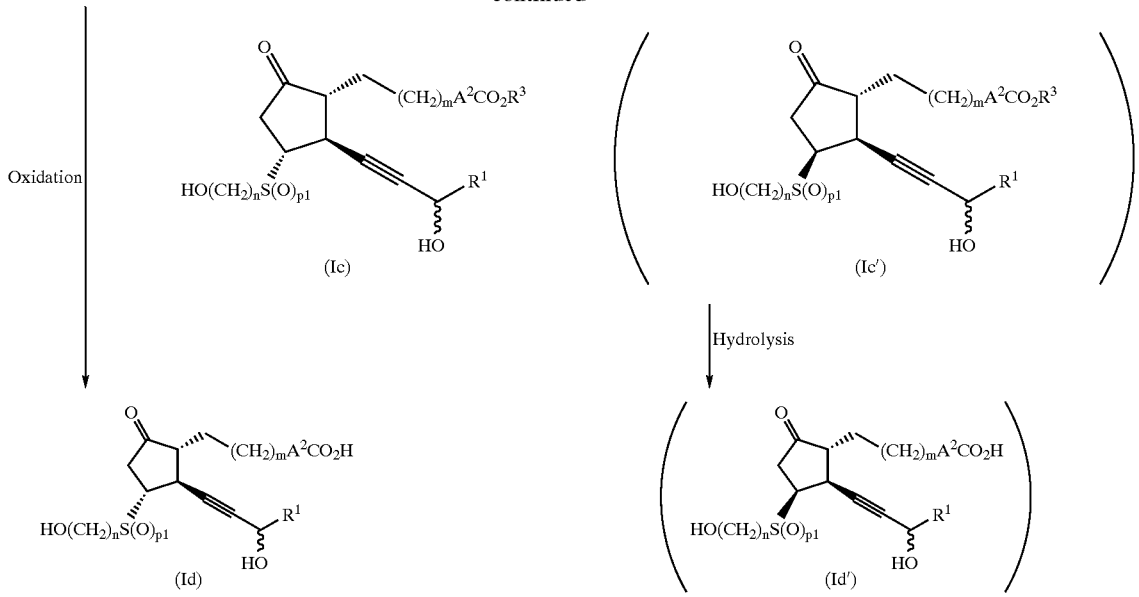

The production processes of the compounds of the present invention are below illustrated according to the reaction scheme.

(1) At first, a compound of Formula (II) is prepared according to the methods described in Japanese Patent No. 2641622 (WO92/18472), Japanese Patent Kokai Nos. 4-818473, 5-117230, 5-294924 or 6-192219 or the modification thereof, it is then subjected to dehydration in an organic solvent (e.g. methanol, ethanol, ethyl acetate or dioxane), water or a mixture thereof by using an organic acid (e.g. formic acid or acetic acid) or an inorganic acid (e.g. sulfuric acid or hydrochloric acid) at a temperature of 0 to 60° C. to give a compound of Formula (III).

(2) The compound of Formula (III) is reacted with a compound of Formula (IV) in an inert solvent (e.g. benzene, toluene, xylene, n-hexane, n-pentane or acetone) at a temperature of −78 to 100° C. to give compounds of formulae (Ia) and (Ia') of the present invention which are stereoisomers at the 11-position. In this reaction, can be optionally added an amine (e.g. triethylamine or diisobutylamine) or a radical generating agent (e.g. azobisisobutyronitrile, azobiscyclohexanecarbonitrile, benzoyl peroxide or triethylborane). These compounds of formulae (Ia) and (Ia') can be purified according to a conventional separation procedure such as column chromatography.

(3) The compound of Formula (Ia) (or (Ia')) is hydrolyzed by an enzyme in a buffer solution such as phosphate buffer or tris-hydrochloride buffer, if necessary, by using an organic solvent (e.g. a water-miscible solvent such as acetone, methanol or ethanol) to give a compound of Formula (Ib) (or (Ib')) of the present invention.

Examples of the enzyme to be used are enzymes produced by microorganisms (e.g. enzymes produced by microorganisms belonging to Candida sp. or Pseudomonas sp.) and enzymes prepared from animal organs (e.g. enzymes prepared from pig liver or pig pancreas). Commercially available enzymes are, for example, lipase VII (derived from microorganism of Candida sp.; Sigma Co.), lipase AY (derived from microorganism of Candida sp.; Amano Pharmaceutical Co.), lipase PS (derived from microorganism of Pseudomonas sp.; Amano Pharmaceutical Co.), lipase MF (derived from microorganism of Pseudomonas sp.; Amano Pharmaceutical Co.), PLE (prepared from pig liver; Sigma Co.), lipase II (prepared from pig pancreas; Sigma Co.) or lipoprotein lipase (prepared from pig pancreas; Tokyo Kasei Kogyo Co.).

The amount of the enzyme to be used, while depending on the potency of the enzyme and the amount of the substrate (the compound of Formula (Ia)), is usually 0.1 to 20 parts by weight based on the substrate, and the reaction temperature is from 25 to 50° C., preferably 30 to 40° C.

(4) The compound of Formula (Ia) or (Ia') is oxidized using an oxidant such as sodium metaperiodate, hydrogen peroxide, peracetic acid, m-chloroperbenzoic acid or tert-butyl hydroxyperoxide in diethyl ether, methanol, ethanol, methylene chloride, water or a mixture thereof at a temperature of −20 to 50° C. to give a compound of Formula (Ic) or (Ic') of the present invention.

(5) The compound of Formula (Ib) or (Ib') is oxidized in the manner similar to as described in the above (4) to give a compound of Formula (Id) or (Id') of the present invention.

The pharmaceutical preparations of the present invention can be administered systemically or topically; orally or parenterally such as rectally, subcutaneously, intramuscularly, intravenously or percutaneously, and preferably orally or intravenously.

The pharmaceutical preparations of the present invention can be produced by containing a pharmaceutically acceptable carrier. Specifically, for oral administration can be prepared the form of tablets, powders, granules, fine powders, capsules, solutions, emulsions or suspensions by mixing an excipient, a binding agent, a disintegrator, a filler, a coating agent or a sugar coating agent, or by mixing an aqueous or non-aqueous solvent according to conventional manners. For intravenous administration can be prepared the form of aqueous or non-aqueous solutions, emulsions, suspensions or solid preparations to be dissolved in a solvent for injection immediately before use according to conventional manners. Furthermore, the compounds of the present invention can be formulated by forming the inclusion compounds with α-, β- or γ-cyclodextrin, or methylated cyclodextrin, and can be administered by injection in the form of aqueous or non-aqueous solutions, emulsions or suspensions.

The dose of the compound of the present invention is varied by the disease, conditions, body weight, age, sex, administration route, etc., but it is preferably from 0.1 ng to 10 mg/day per adult in a single dose or divided doses. When used as a drug for growth inhibition of vascular smooth muscle, the dose is preferably from 1 ng to 1 mg/day per adult in a single or divided doses.

Representative compounds of Formula (I) of the present invention are as described follows:

| Compound | A | m | n | p | $R^1$ | $R^2$ | 11-position | 15-OH |
|---|---|---|---|---|---|---|---|---|
| 1 | $CH_2CH_2$ | 2 | 2 | 0 | (R)-2-methylhexyl | methyl | α | α |
| 2 | $CH_2CH_2$ | 2 | 2 | 0 | (R)-2-methylhexyl | hydrogen | α | α |
| 3 | $CH_2CH_2$ | 3 | 2 | 0 | (R)-2-methylhexyl | tert-butyl | α | α |
| 4 | $CH_2CH_2$ | 3 | 2 | 0 | (R)-2-methylhexyl | tert-butyl | β | α |
| 5 | $CH_2CH_2$ | 3 | 2 | 0 | (R)-2-methylhexyl | methyl | α | α |
| 6 | $CH_2CH_2$ | 3 | 2 | 0 | (R)-2-methylhexyl | methyl | β | α |
| 7 | $CH_2CH_2$ | 3 | 2 | 0 | (R)-2-methylhexyl | hydrogen | α | α |
| 8 | $CH_2CH_2$ | 3 | 2 | 0 | (R)-2-methylhexyl | hydrogen | β | α |
| 9 | $CH_2CH_2$ | 3 | 2 | 0 | (R)-2-methylhexyl | methyl | α | β |
| 10 | $CH_2CH_2$ | 3 | 2 | 0 | (R)-2-methylhexyl | methyl | β | β |
| 11 | $CH_2CH_2$ | 3 | 2 | 0 | (R)-2-methylhexyl | hydrogen | α | β |
| 12 | $CH_2CH_2$ | 3 | 2 | 0 | (R)-2-methylhexyl | hydrogen | β | β |
| 13 | $CH_2CH_2$ | 3 | 3 | 0 | (R)-2-methylhexyl | methyl | α | α |
| 14 | $CH_2CH_2$ | 3 | 3 | 0 | (R)-2-methylhexyl | methyl | β | α |
| 15 | $CH_2CH_2$ | 3 | 3 | 0 | (R)-2-methylhexyl | hydrogen | α | α |
| 16 | $CH_2CH_2$ | 3 | 3 | 0 | (R)-2-methylhexyl | hydrogen | β | α |
| 17 | $CH_2CH_2$ | 4 | 2 | 0 | (R)-2-methylhexyl | methyl | α | α |
| 18 | $CH_2CH_2$ | 4 | 2 | 0 | (R)-2-methylhexyl | hydrogen | α | α |
| 19 | $CH_2CH_2$ | 2 | 2 | 0 | (S)-2-methylhexyl | methyl | α | α |
| 20 | $CH_2CH_2$ | 2 | 2 | 0 | (S)-2-methylhexyl | methyl | β | α |
| 21 | $CH_2CH_2$ | 2 | 2 | 0 | (S)-2-methylhexyl | hydrogen | α | α |
| 22 | $CH_2CH_2$ | 2 | 2 | 0 | (S)-2-methylhexyl | hydrogen | β | α |
| 23 | $CH_2CH_2$ | 2 | 2 | 0 | (S)-2-methylhexyl | hydrogen | α | β |
| 24 | $CH_2CH_2$ | 3 | 2 | 0 | (R)-1-methylhexyl | hydrogen | α | α |
| 25 | $CH_2CH_2$ | 3 | 2 | 0 | (S)-1-methylhexyl | hydrogen | α | α |
| 26 | $CH_2CH_2$ | 3 | 2 | 0 | (S)-2,6-dMe-5-Hp | cyclohexyl | α | α |
| 27 | $CH_2CH_2$ | 3 | 2 | 0 | (S)-2,6-dMe-5-Hp | methyl | α | α |
| 28 | $CH_2CH_2$ | 3 | 2 | 0 | (S)-2,6-dMe-5-Hp | hydrogen | α | α |
| 29 | $CH_2CH_2$ | 3 | 2 | 0 | (S)-2,6-dMe-5-Hp | hydrogen | α | β |
| 30 | $CH_2CH_2$ | 3 | 2 | 0 | (RS)-1-methyl-3-hexynyl | methyl | α | α |
| 31 | $CH_2CH_2$ | 3 | 2 | 0 | (RS)-1-methyl-3-hexynyl | methyl | β | α |
| 32 | $CH_2CH_2$ | 3 | 2 | 0 | (RS)-1-methyl-3-hexynyl | hydrogen | α | α |
| 33 | $CH_2CH_2$ | 3 | 2 | 0 | (S)-1-methyl-3-hexynyl | methyl | α | α |
| 34 | $CH_2CH_2$ | 3 | 2 | 0 | (S)-1-methyl-3-hexynyl | methyl | β | α |
| 35 | $CH_2CH_2$ | 3 | 2 | 0 | (S)-1-methyl-3-hexynyl | hydrogen | α | α |
| 36 | $CH_2CH_2$ | 3 | 2 | 0 | (R)-1-methyl-3-hexynyl | methyl | α | α |
| 37 | $CH_2CH_2$ | 3 | 2 | 0 | (R)-1-methyl-3-hexynyl | hydrogen | α | α |
| 38 | $CH_2CH_2$ | 3 | 2 | 0 | cyclohexyl | methyl | α | α |
| 39 | $CH_2CH_2$ | 3 | 2 | 0 | cyclohexyl | methyl | β | α |
| 40 | $CH_2CH_2$ | 3 | 2 | 0 | cyclohexyl | hydrogen | α | α |
| 41 | $CH_2CH_2$ | 3 | 2 | 0 | cyclohexylmethyl | methyl | α | α |
| 42 | $CH_2CH_2$ | 3 | 2 | 0 | cyclohexylmethyl | methyl | β | α |
| 43 | $CH_2CH_2$ | 3 | 2 | 0 | cyclohexylmethyl | hydrogen | α | α |
| 44 | CH=CH(E) | 3 | 2 | 0 | (R)-2-methylhexyl | methyl | α | α |
| 45 | CH=CH(E) | 3 | 2 | 0 | (R)-2-methylhexyl | hydrogen | α | α |
| 46 | CH=CH(E) | 3 | 2 | 0 | (R)-2-methylhexyl | methyl | β | α |
| 47 | CH=CH(E) | 3 | 2 | 0 | (R)-2-methylhexyl | hydrogen | β | α |
| 48 | CH=CH(Z) | 3 | 2 | 0 | (S)-2-methylhexyl | methyl | α | α |
| 49 | CH=CH(E) | 3 | 2 | 0 | (S)-2-methylhexyl | hydrogen | α | α |
| 50 | CH=CH(E) | 3 | 2 | 0 | (S)-2-methylhexyl | hydrogen | β | α |
| 51 | CH=CH(Z) | 3 | 2 | 0 | (R)-2,6-dMe-5-Hp | hydrogen | α | α |
| 52 | CH=CH(E) | 3 | 2 | 0 | (R)-2-methylpentyl | methyl | α | α |
| 53 | CH=CH(E) | 3 | 2 | 0 | (R)-2-methylpentyl | methyl | β | α |
| 54 | CH=CH(E) | 3 | 2 | 0 | (R)-2-methylpentyl | hydrogen | α | α |
| 55 | CH=CH(E) | 3 | 2 | 0 | 2-methylpropyl | methyl | α | α |
| 56 | CH=CH(E) | 3 | 2 | 0 | 2-methylpropyl | methyl | β | α |
| 57 | CH=CH(E) | 3 | 2 | 0 | 2-methylpropyl | hydrogen | α | α |
| 58 | C≡C | 3 | 2 | 0 | (R)-2-methylhexyl | methyl | α | α |
| 59 | C≡C | 3 | 2 | 0 | (R)-2-methylhexyl | methyl | β | α |
| 60 | C≡C | 3 | 2 | 0 | (R)-2-methylhexyl | hydrogen | α | α |
| 61 | C≡C | 3 | 2 | 0 | (R)-2-methylhexyl | hydrogen | β | α |
| 62 | C≡C | 3 | 2 | 0 | (S)-2-methylhexyl | methyl | α | α |
| 63 | C≡C | 3 | 2 | 0 | (S)-2-methylhexyl | hydrogen | α | α |
| 64 | C≡C | 3 | 2 | 0 | (S)-2-methylhexyl | methyl | α | β |
| 65 | C≡C | 3 | 2 | 0 | (S)-2-methylhexyl | hydrogen | α | β |
| 66 | C≡C | 3 | 2 | 0 | (R)-1-methylhexyl | hydrogen | α | α |
| 67 | C≡C | 3 | 2 | 0 | (S)-1-methylhexyl | hydrogen | α | α |
| 68 | C≡C | 3 | 2 | 0 | 2,2-dimethylhexyl | hydrogen | α | α |
| 69 | C≡C | 3 | 2 | 0 | 2,2-dimethylhexyl | hydrogen | β | α |
| 70 | $OCH_2$ | 3 | 2 | 0 | (R)-2-methylhexyl | methyl | α | α |

-continued

| Compound | A | m | n | p | R¹ | R² | 11-position | 15-OH |
|---|---|---|---|---|---|---|---|---|
| 71 | OCH$_2$ | 3 | 2 | 0 | (R)-2-methylhexyl | methyl | β | α |
| 72 | OCH$_2$ | 3 | 2 | 0 | (R)-2-methylhexyl | methyl | α | β |
| 73 | OCH$_2$ | 3 | 2 | 0 | (R)-2-methylhexyl | methyl | β | β |
| 74 | OCH$_2$ | 3 | 2 | 0 | (R)-2-methylhexyl | hydrogen | α | α |
| 75 | OCH$_2$ | 3 | 2 | 1 | (R)-2-methylhexyl | methyl | α | α |
| 76 | OCH$_2$ | 3 | 2 | 0 | (R)-2-methylhexyl | hydrogen | α | β |
| 77 | OCH$_2$ | 3 | 2 | 2 | (R)-2-methylhexyl | methyl | α | α |
| 78 | OCH$_2$ | 3 | 2 | 0 | (S)-2-methylhexyl | methyl | α | α |
| 79 | OCH$_2$ | 3 | 2 | 0 | (S)-2-methylhexyl | methyl | β | α |
| 80 | OCH$_2$ | 3 | 2 | 0 | (S)-2-methylhexyl | methyl | α | β |
| 81 | OCH$_2$ | 3 | 2 | 0 | (S)-2-methylhexyl | methyl | β | β |
| 82 | OCH$_2$ | 3 | 2 | 0 | (S)-2-methylhexyl | hydrogen | α | α |
| 83 | OCH$_2$ | 3 | 2 | 0 | (S)-2-methylhexyl | hydrogen | β | α |
| 84 | OCH$_2$ | 3 | 2 | 0 | (S)-2-methylhexyl | hydrogen | α | β |
| 85 | O(CH$_2$)$_2$ | 2 | 2 | 0 | (R)-2-methylhexyl | methyl | α | α |
| 86 | O(CH$_2$)$_2$ | 2 | 2 | 0 | (R)-2-methylhexyl | methyl | β | α |
| 87 | O(CH$_2$)$_2$ | 2 | 2 | 0 | (R)-2-methylhexyl | hydrogen | α | α |
| 88 | OCH$_2$ | 3 | 2 | 0 | (R)-1-methyl-3-hexynyl | hydrogen | α | α |
| 89 | OCH$_2$ | 3 | 2 | 0 | (S)-2,6-dMe-5-Hp | methyl | α | α |
| 90 | OCH$_2$ | 3 | 2 | 0 | (S)-2,6-dMe-5-Hp | methyl | β | α |
| 91 | OCH$_2$ | 3 | 2 | 0 | (S)-2,6-dMe-5-Hp | hydrogen | α | α |
| 92 | OCH$_2$ | 3 | 2 | 0 | (R)-2,6-dMe-5-Hp | methyl | α | α |
| 93 | OCH$_2$ | 3 | 2 | 0 | (R)-2,6-dMe-5-Hp | methyl | β | α |
| 94 | OCH$_2$ | 3 | 2 | 0 | (R)-2,6-dMe-5-Hp | hydrogen | α | α |
| 95 | OCH$_2$ | 3 | 2 | 0 | n-pentyl | methyl | α | α |
| 96 | OCH$_2$ | 3 | 2 | 0 | n-pentyl | methyl | β | α |
| 97 | OCH$_2$ | 3 | 2 | 0 | n-pentyl | hydrogen | α | α |
| 98 | SCH$_2$ | 3 | 2 | 0 | (R)-2-methylhexyl | methyl | α | α |
| 99 | SCH$_2$ | 3 | 2 | 0 | (R)-2-methylhexyl | methyl | β | α |
| 100 | SCH$_2$ | 3 | 2 | 0 | (R)-2-methylhexyl | hydrogen | α | α |
| 101 | OCH$_2$ | 3 | 2 | 0 | (S)-1-methylhexyl | methyl | α | α |
| 102 | OCH$_2$ | 3 | 2 | 0 | (S)-1-methylhexyl | methyl | β | α |
| 103 | OCH$_2$ | 3 | 2 | 0 | (S)-1-methylhexyl | hydrogen | α | α |
| 104 | OCH$_2$ | 3 | 2 | 0 | (R)-1-methylhexyl | methyl | α | α |
| 105 | OCH$_2$ | 3 | 2 | 0 | (R)-1-methylhexyl | methyl | β | α |
| 106 | OCH$_2$ | 3 | 2 | 0 | (R)-1-methylhexyl | hydrogen | α | α |
| 107 | OCH$_2$ | 3 | 2 | 0 | 1,1-dimethylpentyl | methyl | α | α |
| 108 | OCH$_2$ | 3 | 2 | 0 | 1,1-dimethylpentyl | methyl | β | α |
| 109 | OCH$_2$ | 3 | 2 | 0 | 1,1-dimethylpentyl | hydrogen | α | α |
| 110 | SCH$_2$ | 3 | 2 | 0 | (R)-2,6-dMe-5-Hp | hydrogen | α | β |
| 111 | SCH$_2$ | 3 | 2 | 0 | (S)-1-methyl-3-hexynyl | hydrogen | α | α |
| 112 | SCH$_2$ | 3 | 2 | 0 | (S)-1-methyl-3-hexynyl | hydrogen | α | β |
| 113 | SCH$_2$ | 3 | 2 | 0 | (R)-1-methyl-3-hexynyl | hydrogen | α | α |
| 114 | SCH$_2$ | 3 | 2 | 0 | (R)-1-methyl-3-hexynyl | hydrogen | α | β |
| 115 | S(O)CH$_2$ | 3 | 2 | 1 | (S)-1-methyl-3-hexynyl | hydrogen | α | α |
| 116 | S(O)$_2$CH$_2$ | 3 | 2 | 2 | (R)-1-methyl-3-hexynyl | hydrogen | α | α |
| 117 | S(CH$_2$)$_2$ | 2 | 2 | 0 | (R)-2-methylhexyl | hydrogen | α | α |
| 118 | S(O)(CH$_2$)$_2$ | 2 | 2 | 1 | (R)-2-methylhexyl | hydrogen | α | α |
| 119 | CH=CH(E) | 3 | 2 | 0 | (R)-5-OH-2-methylpentyl | methyl | α | α |
| 120 | CH=CH(E) | 3 | 2 | 1 | (R)-5-OH-2-methylpentyl | methyl | α | α |
| 121 | CH=CH(E) | 3 | 2 | 0 | (R)-5-OH-2-methylpentyl | methyl | β | α |
| 122 | CH=CH(E) | 3 | 2 | 0 | (R)-5-OH-2-methylpentyl | hydrogen | α | α |
| 123 | CH=CH(E) | 3 | 2 | 1 | (R)-5-OH-2-methylpentyl | hydrogen | α | α |
| 124 | CH=CH(E) | 3 | 2 | 0 | (R)-5-OMe-2-methylpentyl | methyl | α | α |
| 125 | CH=CH(E) | 3 | 2 | 2 | (R)-5-OMe-2-methylpentyl | methyl | α | α |
| 126 | CH=CH(E) | 3 | 2 | 0 | (R)-5-OMe-2-methylpentyl | methyl | β | α |
| 127 | CH=CH(E) | 3 | 2 | 1 | (R)-5-OMe-2-methylpentyl | methyl | β | α |
| 128 | CH=CH(E) | 3 | 2 | 0 | (R)-5-OMe-2-methylpentyl | hydrogen | α | α |
| 129 | CH=CH(E) | 3 | 2 | 1 | (R)-5-OMe-2-methylpentyl | hydrogen | α | α |
| 130 | CH=CH(E) | 3 | 2 | 2 | (R)-5-OMe-2-methylpentyl | hydrogen | α | α |

2,6-dMe-5-Hp: 2,6-dimethyl-5-heptenyl, 5-OH-2-methylpentyl:5-hydroxy-2-methylpentyl, 5-OMe-2-methylpentyl:5-methoxy-2-methylpentyl
11-position: the bond between S(O)$_p$(CH$_2$)$_n$OH group and the carbon atom of the cyclopentane ring
15-position: the bond between the carbon atom attached to R¹ and OH group.
CH=CH(E): trans-vinylene
CH=CH(Z): cis-vinylene

BEST MODE FOR CARRYING OUT THE INVENTION

The present invention is illustrated in more detail by the following examples and experiment, but not limited thereof. In the nomenclature of the compound, "nor" means the lack of the carbon chain at the position (e.g. 17,18,19,20-tetranor means the lack of carbon chains from the 17- to 20-positions).

EXAMPLE 1

(11R,17R)-11-deoxy-11-(2-hydroxyethylthio)-17,20-dimethyl-13,14-didehydro-PGE$_1$ Methyl Ester (Compound 5) and (11S,17R)-11-deoxy-11-(2-hydroxyethylthio)-17,20-dimethyl-13,14-didehydro-PGE$_1$ Methyl Ester (Compound 6)

(1) To an ethyl acetate solution (37 ml) of (17R)-17,20-dimethyl-13,14-didehydro-PGE$_1$ methyl ester (370 mg, 0.94 mmol) was added an ethyl acetate solution (4M, 2.8 ml, 11.3 mmol) of hydrochloric acid at room temperature, followed by stirring for 1.5 hours. The reaction solution was neutralized with a saturated aqueous sodium bicarbonate solution, and the organic layer was separated, washed with a saturated aqueous sodium chloride solution, dried over anhydrous magnesium sulfate and filtered. The filtrate was concentrated under reduced pressure, and the resulting crude product was purified by a silica gel column chromatography (developing solvent; hexane:ethyl acetate=3:1) to give (17R)-17,20-dimethyl-13,14-didehydro-PGA$_1$ methyl ester (230 mg).

$^1$H-NMR(CDCl$_3$,200 MHz) δ ppm; 0.82–1.01(m,6H), 1.04–2.00(m,20H), 2.21–2.48(m,1H), 2.32(t,J=7.4 Hz,2H), 3.40–3.47(m,1H), 3.67(s,3H), 4.39–4.50(m,1H), 6.18(dd,J=5.7,2.4 Hz,1H), 7.47(dd,J=5.7,2.4 Hz,1H)

IR(neat) cm$^{-1}$; 3438,2930,2858,2209,1739,1715,1592, 1463,1438,1379,1199, 1174,1065,885,599

(2) To a chloroform solution (2.9 ml) of the compound obtained in the above (1) (220 mg, 0.58 mmol) were added 2-mercaptoethanol (82 μl, 1.19 mmol) and diisopropylamine (16 μl, 0.12 mmol), followed by stirring at room temperature overnight. The reaction solution was applied to a short silica gel column chromatography (developing solvent; ethyl acetate), and the resulting crude product was purified by a silica gel column chromatography (developing solvent; hexane:ethyl acetate=1:1) to give (11R,17R)-11-deoxy-11-(2-hydroxyethylthio)-17,20-dimethyl-13,14-didehydro-PGE$_1$ methyl ester (106 mg) and (11S,17R)-11-deoxy-11-(2-hydroxyethylthio)-17,20-dimethyl-13,14-didehydro-PGE$_1$ methyl ester (136 mg).

(11R,17R)-11-deoxy-11-(2-hydroxyethylthio)-17,20-dimethyl-13,14-didehydro-PGE$_1$ Methyl Ester $^1$H-NMR(CDCl$_3$,200 MHz) δ ppm; 0.84–1.04(m,6H), 1.08–2.01(m,21H), 2.11(dd,J=18.7,11.9 Hz,1H), 2.17–2.41(m,1H), 2.31(t,J=7.4 Hz,2H), 2.57–3.02(m,3H), 3.07–3.37(m,2H), 3.67(s,3H), 3.79–3.92(m,2H), 4.37–4.53(m,1H)

IR(neat) cm$^{-1}$; 3431,2929,2859,2231,1742,1438,1380, 1201,1159,1049,772

(11S,17R)-11-deoxy-11-(2-hydroxyethylthio)-17,20-dimethyl-13,14-didehydro-PGE$_1$ Methyl Ester $^1$H-NMR(CDCl$_3$,200 MHz) δ ppm; 0.82–1.02(m,6H), 1.06–1.90(m,21H), 2.31(t,J=7.4 Hz,2H), 2.43–2.69(m,3H), 2.85–3.15(m,3H), 3.56–3.88(m,3H), 3.67(s,3H), 4.42–4.55 (m,1H)

IR(neat) cm$^{-1}$; 3432,2930,2858,2234,1741,1462,1438, 1383,1282,1201,1166, 1048,728

EXAMPLE 2

(11R,17R)-11-deoxy-11-(2-hydroxyethylthio)-17,20-dimethyl-13,14-didehydro-PGE$_1$ (Compound 7)

To an acetone solution (0.55 ml) of (11R,17R)-11-deoxy-11-(2-hydroxyethylthio)-17,20-dimethyl-13,14-didehydro-PGE$_1$ methyl ester obtained in Example 1 (100 mg, 0.22 mmol) were added water (5.5 ml), phosphate buffer (pH 8.0) (0.2 M, 5.5 ml) and PLE (manufactured by Sigma Co., 2.53 unit/μl, aqueous ammonium sulfate solution, 87 μl), followed by stirring at room temperature for 2 days. After adjustment of the pH to 4 with 1M hydrochloric acid, the reaction solution was salted out with ammonium sulfate, and extracted with ethyl acetate, and the organic layer was washed with a saturated aqueous sodium chloride solution, dried over anhydrous magnesium sulfate and filtered. The filtrate was concentrated under reduced pressure, and the resulting crude product was purified by a silica gel column chromatography (developing solvent; hexane:ethyl acetate=1:2) to give the title compound (76 mg).

$^1$H-NMR(CDCl$_3$,300 MHz) δ ppm; 0.81–0.99(m,6H), 1.02–1.81(m,19H), 2.11(dd,J=18.9,11.8 Hz,1H), 2.20–2.39 (m,1H), 2.35(t,J=7.3 Hz,2H), 2.61–3.36(m,8H), 3.79–3.95 (m,2H), 4.38–4.52(m,1H)

IR(neat) cm$^{-1}$; 3392,2929,2858,2235,1741,1713,1463, 1403,1283,1158,1048,728

EXAMPLE 3

(11S,17R)-11-deoxy-11-(2-hydroxyethylthio)-17,20-dimethyl-13,14-didehydro-PGE$_1$ (Compound 8)

Following the substantially same manner as in Example 2 using (11S,17R)-11-deoxy-11-(2-hydroxyethylthio)-17,20-dimethyl-13,14-didehydro-PGE$_1$ methyl ester obtained in Example 1, thereby the title compound was obtained.

$^1$H-NMR(CDCl$_3$,300 MHz) δ ppm; 0.81–1.00(m,6H), 1.06–1.82(m,22H), 2.35(t,J=7.0 Hz,2H), 2.44–2.68(m,3H), 2.86–3.13(m,3H), 3.57–3.95(m,3H), 4.39–4.53(m,1H)

IR(neat) cm$^{-1}$; 3392,2930,2858,2233,1739,1714,1637, 1464,1403,1380,1285, 1163,1049,728,605

EXAMPLE 4

(11R,16RS)-11-deoxy-11-(2-hydroxyethylthio)-16, 20-dimethyl-13,14,18,18,19,19-hexadehydro-PGE$_1$ Methyl Ester (Compound 30) and (11S,16RS)-11-deoxy-11-(2-hydroxyethylthio)-16,20-dimethyl-13, 14,18,18,19,19-hexadehydro-PGE$_1$ Methyl Ester (Compound 31)

(1) Following the substantially same manner as in Example 1(1) using (16RS)-16,20-dimethyl-13,14,18,18,19, 19-hexadehydro-PGE$_1$ methyl ester in place of (17R)-17, 20-dimethyl-13,14-didehydro-PGE$_1$ methyl ester in Example 1(1), thereby (16RS)-16,20-dimethyl-13,14,18,18, 19,19-hexadehydro-PGA$_1$ methyl ester was obtained.

$^1$H-NMR(CDCl$_3$,300 MHz) δ ppm; 1.02–1.16(m,3H), 1.12(t,J=7.4 Hz,3H), 1.20–2.46(m,17H), 2.31(t,J=7.5 Hz,2H), 3.42–3.48(m,1H), 3.67(s,3H), 4.37–4.47(m,1H), 6.19(dd,J=5.6,2.3 Hz,1H),7.48(dd,J=5.6,2.4 Hz,1H)

IR(neat) cm$^{-1}$; 3453,2934,2858,2213,1734,1713,1591, 1456,1437,1346,1320, 1200,1174,1098,1027,984,885,606

(2) Following the substantially same manner as in Example 1(2) using the compound obtained in the above (1), thereby the title compounds were obtained.

(11R,16RS)-11-deoxy-11-(2-hydroxyethylthio)-16, 20-dimethyl-13,14,18,18,19,19-hexadehydro-PGE$_1$ Methyl Ester $^1$H-NMR(CDCl$_3$,300 MHz) δ ppm; 1.08(d,J=6.9 Hz,3/2H), 1.09(d,J=6.7 Hz,3/2H), 1.12(t,J=7.3 Hz,3H), 1.24–2.34 (m,17H), 2.30(t,J=7.4 Hz,2H), 2.50–3.00(m,5H), 3.13(dt,J=13.8,6.9 Hz,1H), 3.23–3.35(m,1H), 3.67(s,3H), 3.80–3.90 (m,2H), 4.37–4.48(m,1H)

IR(neat) cm$^{-1}$; 3400,2932,2858,2242,1740,1436,1376, 1320,1278,1205,1169, 1097,1022

(11S,16RS)-11-deoxy-11-(2-hydroxyethylthio)-16, 20-dimethyl-13,14,18,18,19,19-hexadehydro-PGE$_1$ Methyl Ester $^1$H -NMR(CDCl$_3$,300 MHz) δ ppm; 1.08(d,J=7.1 Hz,3/2H), 1.10(d,J=6.7 Hz,3/2H), 1.12(t,J=7.5 Hz,3H),1.18–3.16

(m,23H), 2.30(t,J=7.4 Hz,2H), 3.58–3.68(m,1H), 3.67(s, 3H), 3.75–3.84(m,2H), 4.40–4.49(m,1H)

IR(neat) cm$^{-1}$; 3437,2933,2858,2233,1739,1456,1437, 1375,1320,1281,1202, 1167,1024

EXAMPLE 5

(11R,16RS)-11-deoxy-11-(2-hydroxyethylthio)-16, 20-dimethyl-13,14,18,18,19,19-hexadehydro-PGE$_1$ (Compound 32)

Following the substantially same manner as in Example 2 using (11R,16RS)-11-deoxy-11-(2-hydroxyethylthio)-16, 20-dimethyl-13,14,18,18,19,19-hexadehydro-PGE$_1$ methyl ester obtained in Example 4, thereby the title compound was obtained.

$^1$H-NMR(CDCl$_3$,300 MHz) δ ppm; 1.08(d,J=6.9 Hz,3/2H), 1.10(d,J=6.7 Hz,3/2H), 1.12(t,J=7.5 Hz,3H),1.22–2.46 (m,20H), 2.35(t,J=7.3 Hz,2H), 2.63–2.93(m,3H), 3.07–3.18 (m,1H), 3.23–3.36(m,1H), 3.85(t,J=6.5 Hz,2H), 4.40–4.48 (m,1H)

IR(neat) cm$^{-1}$; 3392,2933,2858,2235,1741,1458,1403, 1320,1282,1157,1096, 1019,935,725,624

EXAMPLE 6

(11R)-11-deoxy-11-(2-hydroxyethylthio)-16,17,18, 19,20-pentanor-15-cyclohexyl-13,14-didehydro-PGE$_1$ Methyl Ester (Compound 38) and (11S)-11-deoxy-11-(2-hydroxyethylthio)-16,17,18,19,20-pentanor-15-cyclohexyl-13,14-didehydro-PGE$_1$ Methyl Ester (Compound 39)

(1) Following the substantially same manner as in Example 1(1) using 16,17,18,19,20-pentanor-15-cyclohexyl-13,14-didehydro-PGE$_1$ methyl ester in place of (17R)-17,20-dimethyl-13,14-didehydro-PGE$_1$ methyl ester in Example 1(1), thereby 16,17,18,19,20-pentanor-15-cyclohexyl-13,14-didehydro-PGA$_1$ methyl ester was obtained.

$^1$H-NMR(CDCl$_3$,200 MHz) δ ppm; 0.97–2.00(m,22H), 2.20–2.46(m,1H), 2.31(t,J=7.4 Hz,2H), 3.40–3.49(m,1H), 3.67(s,3H),4.11–4.21(m,1H), 6.19(dd,J=5.7,2.4 Hz,1H), 7.48(dd,J=5.7,2.4 Hz,1H)

IR(neat) cm$^{-1}$; 3437,2929,2855,2213,1738,1713,1450, 1346,1198,1174,1097, 1017,893

(2) Following the substantially same manner as in Example 1(2) using the compound obtained in the above (1), thereby the title compounds were obtained.

(11R)-11-deoxy-11-(2-hydroxyethylthio)-16,17,18, 19,20-pentanor-15-cyclohexyl-13,14-didehydro-PGE$_1$ Methyl Ester $^1$H-NMR(CDCl$_3$,200 MHz) δ ppm; 0.94–1.98(m,21H), 2.12(dd,J=18.8,11.8 Hz,1H), 2.18–2.40(m,1H), 2.31(t,J=7.4 Hz,2H), 2.48–2.98(m,5H), 3.06–3.38(m,2H), 3.68(s,3H), 3.86(t,J=6.2 Hz,2H),4.12–4.26(m,1H)

IR(neat) cm$^{-1}$: 3426,2928,2854,1740,1450,1260,1206, 1171,1044,1013,893, 725,594

(11S)-11-deoxy-11-(2-hydroxyethylthio)-16,17,18, 19,20-pentanor-15-cyclohexyl-13,14-didehydro-PGE$_1$ Methyl Ester $^1$H-NMR(CDCl$_3$,200 MHz) δ ppm; 0.90–1.94(m,21H), 2.31(t,J=7.4 Hz,2H), 2.36–3.17(m,5H), 3.11(ddd,J=9.8,5.4, 1.8 Hz,1H), 3.56–4.01(m,5H),3.67(s,3H), 4.09–4.26(m,1H)

IR(neat) cm$^{-1}$: 3410,2928,2854,1739,1638,1450,1401, 1278,1207,1169,1046, 1014,893,726,580

EXAMPLE 7

(11R)-11-deoxy-11-(2-hydroxyethylthio)-16,17,18, 19,20-pentanor-15-cyclohexyl-13,14-didehydro-PGE$_1$ (Compound 40)

Following the substantially same manner as in Example 2 using (11R)-11-deoxy-11-(2-hydroxyethylthio)-16,17,18, 19,20-pentanor-15-cyclohexyl-13,14-didehydro-PGE$_1$ methyl ester obtained in Example 6, thereby the title compound was obtained.

$^1$H-NMR(CDCl$_3$,300 MHz) δ ppm; 0.96–1.91(m,23H), 2.12(dd,J=18.7,11.7 Hz,1H), 2.22–2.39(m,1H), 2.35(t,J=7.3 Hz,2H),2.62–2.98(m,4H), 3.14(dt,J=13.8,6.6 Hz,1H), 3.29 (ddd,J=11.7,10.4,8.1 Hz,1H), 3.85(t,J=6.6 Hz,2H), 4.18(dd, J=6.0,1.8 Hz,1H)

IR(neat) cm$^{-1}$: 3399,2928,2854,1740,1450,1402,1278, 1157,1044,1011,956,893,757, 596

EXAMPLE 8

(11R)-11-deoxy-11-(2-hydroxyethylthio)-17,18,19, 20-tetranor-16-cyclohexyl-13,14-didehydro-PGE$_1$ Methyl Ester (Compound 41) and (11S)-11-deoxy-11-(2-hydroxyethylthio)-17,18,19,20-tetranor-16-cyclohexyl-13,14-didehydro-PGE$_1$ Methyl Ester (Compound 42)

(1) Following the substantially same manner as in Example 1(1) using 17,18,19,20-tetranor-16-cyclohexyl-13, 14-didehydro-PGE$_1$ methyl ester in place of (17R)-17,20-dimethyl-13,14-didehydro-PGE$_1$ methyl ester in Example 1(1), thereby 17,18,19,20-tetranor-16-cyclohexyl-13,14-didehydro-PGA$_1$ methyl ester was obtained.

$^1$H-NMR(CDCl$_3$,200 MHz) δ ppm; 0.82–1.98(m,24H), 2.23–2.46(m,1H), 2.32(t,J=7.4 Hz,2H), 3.38–3.49(m,1H), 3.68(s,3H),4.35–4.55(m,1H), 6.19(dd,J=5.7,2.4 Hz,1H), 7.48(dd,J=5.7,2.4 Hz,1H)

IR(neat) cm$^{-1}$; 3448,2925,2853,1739,1713,1448,1347, 1200,1174,1099,887

(2) Following the substantially same manner as in Example 1(2) using the compound obtained in the above (1), thereby the title compounds were obtained.

(11R)-11-deoxy-11-(2-hydroxyethylthio)-17,18,19, 20-tetranor-16-cyclohexyl-13,14-didehydro-PGE$_1$ Methyl Ester $^1$H-NMR(CDCl$_3$,300 MHz) δ ppm; 0.85–1.82(m,24H), 2.11(dd,J=18.9,11.8 Hz,1H), 2.22–2.35(m,1H), 2.31(t,J=7.4 Hz,2H),2.60–2.93(m,2H), 2.79(ddd,J=18.9,8.0,1.4 Hz,1H), 2.87(dt,J=14.0,6.2 Hz,1H), 3.14(dt,J=14.0,6.6 Hz,1H), 3.27 (ddd,J=11.8,10.4,8.0 Hz,1H), 3.67(s,3H), 3.86(dd,J=6.6,6.2 Hz,2H), 4.39–4.53(m,1H)

IR(neat) cm$^{-1}$; 3400,2924,2852,1740,1447,1348,1261, 1201,1170,1045,895,725

(11S)-11-deoxy-11-(2-hydroxyethylthio)-17,18,19, 20-tetranor-16-cyclohexyl-13,14-didehydro-PGE$_1$ Methyl Ester $^1$H-NMR(CDCl$_3$,300 MHz) δ ppm; 0.82–1.88(m,23H), 2.13–3.04(m,7H), 2.31(t,J=7.4 Hz,2H), 3.10(ddd,J=9.8,5.3, 1.8 Hz,1H), 3.62(ddd,J=7.1,5.3,3.9 Hz,1H), 3.67(s,3H), 3.74–3.96(m,2H),4.40–4.55(m,1H)

IR(neat) cm$^{-1}$; 3410,2924,2852,1740,1638,1447,1347, 1282,1201,1168,1045, 726,581,430

EXAMPLE 9

(11R)-11-deoxy-11-(2-hydroxyethylthio)-17,18,19, 20-tetranor-16-cyclohexyl-13,14-didehydro-PGE$_1$ (Compound 43)

Following the substantially same manner as in Example 2 using (11R)-11-deoxy-11-(2-hydroxyethylthio)-17,18,19, 20-tetranor-16-cyclohexyl-13,14-didehydro-PGE$_1$ methyl ester obtained in Example 8, thereby the title compound was obtained.

$^1$H-NMR(CDCl$_3$,300 MHz) δ ppm; 0.85–1.82(m,25H), 2.11(dd,J=18.8,11.7 Hz,1H), 2.22–2.39(m,1H),2.35(t,J=7.3 Hz,2H),2.62–2.94(m,3H), 2.87(dt,J=13.8,6.4 Hz,1H), 3.14 (dt,J=13.8,6.6 Hz,1H), 3.28(ddd,J=11.7,10.5,8.0 Hz,1H), 3.86(dd,J=6.6,6.4 Hz,2H), 4.47(dt,J=1.8,7.0 Hz,1H)

IR(neat) cm$^{-1}$; 3378,2924,2853,1740,1448,1402,1347, 1281,1158,1044,896, 757,605

EXAMPLE 10

(2E,11R,17S)-11-deoxy-11-(2-hydroxyethylthio)-17, 20-dimethyl-2,3,13,14-tetradehydro-PGE$_1$ (Compound 49) and (2E,11S,17S)-11-deoxy-11-(2-hydroxyethylthio)-17,20-dimethyl-2,3,13,14-tetradehydro-PGE$_1$ (Compound 50)

(1) Following the substantially same manner as in Example 1(1) using (2E,17S)-17,20-dimethyl-2,3,13,14-tetradehydro-PGE$_1$ in place of (17R)-17,20-dimethyl-13,14-didehydro-PGE$_1$ methyl ester in Example 1(1), thereby (2E,17S)-17,20-dimethyl-2,3,13,14-tetradehydro-PGA$_1$ was obtained.

$^1$H-NMR(CDCl$_3$,300 MHz) δ ppm; 0.78–0.97(m,6H), 1.04–1.97(m,17H), 2.14–2.33(m,2H), 2.34–2.45(m,1H), 3.40–3.46(m,1H), 4.45(dt,J=2.0,7.1 Hz,1H), 5.85(dd,J=15.6,1.6 Hz,1H), 6.19(dd,J=5.7,2.3 Hz,1H), 7.08(dt,J=15.6, 6.9 Hz,1H), 7.47(dd,J=5.7,2.5 Hz,1H)

IR(neat) cm$^{-1}$; 3400,2929,2859,2230,1698,1653,1592, 1542,1460,1418,1379, 1345,1285,1224,1043,983,875,757, 667

(2) Following the substantially same manner as in Example 1(2) using the compound obtained in the above (1), thereby the title compounds were obtained. (2E,11R,17S)-11-deoxy-11-(2-hydroxyethylthio)-17,20-dimethyl-2,3,13, 14-tetradehydro-PGE$_1$ $^1$H-NMR(CDCl$_3$,300 MHz) δ ppm; 0.84–0.95(m,6H), 1.06–1.86(m,15H), 2.03–2.34(m,3H), 2.11(dd,J=18.9,11.7 Hz,1H),2.59–3.67(m,8H), 3.86(t,J=6.5 Hz,2H), 4.46(dt,J=1.8,7.2 Hz,1H), 5.84(dt,J=15.6,1.5 Hz,1H),7.04(dt,J=15.6, 7.1 Hz,1H)

IR(neat) cm$^{-1}$; 3388,2929,2858,2230,1743,1697,1653, 1460,1402,1379,1283, 1158,1045,1017,984,729,670,539, 447

(2E,11S,17S)-11-deoxy-11-(2-hydroxyethylthio)-17, 20-dimethyl-2,3,13,14-tetradehydro-PGE$_1$ $^1$H-NMR(CDCl$_3$,300 MHz) δ ppm; 0.82–0.97(m,6H), 1.05–1.78(m,15H), 2.08–2.82(m,8H), 2.86–3.13(m,3H), 3.59–3.88(m,3H), 4.38–4.53(m,1H), 5.80–5.90(m,1H), 7.05 (dt,J=15.8,7.0 Hz,1H)

IR(neat) cm$^{-1}$; 3389,2929,2858,2230,1739,1696,1653, 1461,1402,1378,1285, 1164,1046,984,729,670

EXAMPLE 11

(11R,17R)-11-deoxy-11-(2-hydroxyethylthio)-17,20-dimethyl-2,2,3,3,13,14-hexadehydro-PGE$_1$ Methyl Ester (Compound 58) and (11S,17R)-11-deoxy-11-(2-hydroxyethylthio)-17,20-dimethyl-2,2,3,3,13,14-hexadehydro-PGE$_1$ Methyl Ester (Compound 59)

(1) Following the substantially same manner as in Example 1(1) using (17R)-17,20-dimethyl-2,2,3,3,13,14-hexadehydro-PGE$_1$ methyl ester in place of (17R)-17,20-dimethyl-13,14-didehydro-PGE$_1$ methyl ester in Example 1(1), thereby (17R)-17,20-dimethyl-2,2,3,3,13,14-hexadehydro-PGA$_1$ methyl ester was obtained.

$^1$H-NMR(CDCl$_3$,300 MHz) δ ppm; 0.82–0.99(m,6H), 1.08–2.00(m,16H), 2.27–2.46(m,3H), 3.41–3.48(m,1H), 3.77(s,3H), 4.33–4.49(m,1H), 6.19(dd,J=5.7,2.3 Hz,1H), 7.48(dd,J=5.7,2.5 Hz,1H)

IR(neat) cm$^{-1}$; 3416,2953,2929,2860,2237,1715,1591, 1459,1435,1379,1258, 1179,1077,819,753,561

(2) Following the substantially same manner as in Example 1(2) using the compound obtained in the above (1), thereby the title compounds were obtained.

(11R,17R)-11-deoxy-11-(2-hydroxyethylthio)-17,20-dimethyl-2,2,3,3,13,14-hexadehydro-PGE$_1$ Methyl Ester $^1$H-NMR(CDCl$_3$,300 MHz) δ ppm; 0.83–1.01(m,3H), 0.94(d,J=6.7 Hz,3H), 1.08–1.84(m,15H), 2.12(dd,J=18.9, 11.8 Hz,1H), 2.22–2.41(m,3H), 2.47–2.94(m,3H), 2.79(ddd, J=18.9,8.0,1.2 Hz,1H), 2.88(dt,J=13.8,6.2 Hz,1H), 3.14(dt, 13.8,6.6 Hz,1H), 3.28(ddd,J=11.8,10.4,8.0 Hz,1H), 3.76(s, 3H), 3.80–3.91(m,2H), 4.39–4.50(m,1H)

IR(neat) cm$^{-1}$; 3409,2953,2929,2869,2236,1745,1714, 1460,1435,1402,1379, 1258,1155,1076,819,753,561

(11S,17R)-11-deoxy-11-(2-hydroxyethylthio)-17,20-dimethyl-2,2,3,3,13,14-hexadehydro-PGE$_1$ Methyl Ester $^1$H-NMR(CDCl$_3$,300 MHz) δ ppm; 0.79–1.02(m,6H), 1.04–1.93(m,16H), 2.24–3.15(m,7H), 3.10(ddd,J=10.1,5.3, 1.7 Hz,1H), 3.60–3.69(m,3H), 3.65(ddd,J=6.9,5.3,3.6 Hz,1H), 3.76(s,3H), 4.37–4.54(m,1H)

IR(neat) cm$^{-1}$; 3410,2953,2927,2858,2236,1743,1712, 1638,1459,1435,1402, 1377,1261,1158,1076,820,753,561

EXAMPLE 12

(11R,17R)-3-oxa-11-deoxy-11-(2-hydroxyethylthio)-17,20-dimethyl-13,14-didehydro-PGE$_1$ Methyl Ester (Compound 70) and (11S,17R)-3-oxa-11-deoxy-11-(2-hydroxyethylthio)-17,20-dimethyl-13,14-didehydro-PGE$_1$ Methyl Ester (Compound 71)

(1) Following the substantially same manner as in Example l(1) using (17R)-3-oxa-17,20-dimethyl-13,14-didehydro-PGE$_1$ methyl ester in place of (17R)-17,20-dimethyl-13,14-didehydro-PGE$_1$ methyl ester in Example 1(1), thereby (17R)-3-oxa-17,20-dimethyl-13,14-didehydro-PGA$_1$ methyl ester was obtained.

$^1$H-NMR(CDCl$_3$,200 MHz) δ ppm; 0.80–2.18(m,22H), 2.35–2.50(m,1H), 3.42–3.65(m,3H),3.76(s,3H),4.09(s,2H), 4.37–4.50(m,1H), 6.19(dd,J=5.7,2.4 Hz,1H), 7.48(dd,J=5.7, 2.4 Hz,1H).

IR(neat) cm$^{-1}$; 3435,2953,2929,2870,1755,1711,1591, 1458,1438,1379,1346, 1286,1212,1139,1061,812,707,582

(2) Following the substantially same manner as in Example 1(2) using the compound obtained in the above (1), thereby the title compounds were obtained.

(11R,17R)-3-oxa-11-deoxy-11-(2-hydroxyethylthio)-17,20-dimethyl-13,14-didehydro-PGE$_1$ Methyl Ester $^1$H-NMR(CDCl$_3$,300 MHz) δ ppm; 0.84–1.86(m,18H), 0.91(t,J=7.0Hz,3H), 2.12(dd,J=18.8,11.9 Hz,1H), 2.22–2.36 (m,1H), 2.40–2.97(m,5H), 3.13(dt,J=13.8,6.6 Hz,1H), 3.27

(ddd,J=11.9,10.3,8.0 Hz,1H), 3.47–3.63(m,2H),3.75(s,3H), 3.78–3.90(m,2H), 4.08(s,2H), 4.37–4.49(m,1H)

IR(neat) cm$^{-1}$; 3435,2953,2929,2870,1745,1458,1439, 1401,1379,1284,1214, 1140,1048,706,593

(11S,17R)-3-oxa-11-deoxy-11-(2-hydroxyethylthio)-17,20-dimethyl-13,14-didehydro-PGE$_1$ Methyl Ester $^1$H-NMR(CDCl$_3$,300 MHz) δ ppm; 0.84–1.82(m,18H), 0.92(t,J=7.1 Hz,3H), 2.35–2.70(m,5H), 2.86–3.05(m,2H), 3.11(ddd,J=9.9,5.3,1.7 Hz,1H), 3.54(t,J=5.8 Hz,2H), 3.59–3.67(m,1H), 3.71–3.86(m,2H), 3.75(s,3H), 4.07(s,2H), 4.41–4.52(m,1H)

IR(neat) cm$^{-1}$; 3435,2953,2929,2870,1745,1638,1459, 1439,1401,1379,1286, 1214,1139,1049,706,579

EXAMPLE 13

(11R,17R)-3-oxa-11-deoxy-11-(2-hydroxyethylthio)-17,20-dimethyl-13,14-didehydro-PGE$_1$ (Compound 74)

Following the substantially same manner as in Example 2 using (11R,17R)-3-oxa-11-deoxy-11-(2-hydroxyethylthio)-17,20-dimethyl-13,14-didehydro-PGE$_1$ methyl ester obtained in Example 12, thereby the title compound was obtained.

$^1$H-NMR(CDCl$_3$,300 MHz) δ ppm; 0.80–1.90(m,18H), 0.92(t,J=7.0 Hz,3H), 2.07–2.93(m,8H), 3.05–3.17(m,1H), 3.22–3.34(m,1H), 3.55–3.65(m,2H), 3.85(t,J=6.2 Hz,2H), 4.08(s,2H), 4.38–4.51(m,1H)

IR(neat) cm$^{-1}$; 3400,2928,2870,2236,1740,1621,1460, 1429,1348,1228,1131, 1049,726,677,542

EXAMPLE 14

(11R,17S)-3-oxa-11-deoxy-11-(2-hydroxyethylthio)-17,20-dimethyl-13,14-didehydro-PGE$_1$ Methyl Ester (Compound 78) and (11S,17S)-3-oxa-11-deoxy-11-(2-hydroxyethylthio)-17,20-dimethyl-13,14-didehydro-PGE$_1$ Methyl Ester (Compound 79)

(1) Following the substantially same manner as in Example 1(1) using (17S)-3-oxa-17,20-dimethyl-13,14-didehydro-PGE$_1$ methyl ester in place of (17R)-17,20-dimethyl-13,14-didehydro-PGE$_1$ methyl ester in Example 1(1), thereby (17S)-3-oxa-17,20-dimethyl-13,14-didehydro-PGA$_1$ methyl ester was obtained.

$^1$H-NMR(CDCl$_3$,200 MHz) δ ppm; 0.84–0.96(m,6H), 1.08–2.10(m,15H), 2.13(d,J=5.9 Hz,1H), 2.38–2.50(m,1H), 3.42–3.62(m,3H), 3.76(s,3H), 4.09(s,2H), 4.35–4.52(m,1H), 6.19(dd,J=5.7,2.2 Hz,1H), 7.47(dd,J=5.7,2.4 Hz,1H)

IR(neat) cm$^{-1}$; 3442,2953,2929,2870,2242,1752,1712, 1591,1459,1439,1378, 1346,1285,1212,1139,1043,811,706, 581

(2) Following the substantially same manner as in Example 1(2) using the compound obtained in the above (1), thereby the title compounds were obtained.

(11R,17S)-3-oxa-11-deoxy-11-(2-hydroxyethylthio)-17,20-dimethyl-13,14-didehydro-PGE$_1$ Methyl Ester $^1$H-NMR(CDCl$_3$,300 MHz) δ ppm; 0.84–0.96(m,6H), 1.09–1.90(m,15H),2.12(dd,J=18.8,11.6 Hz,1H), 2.20–2.36 (m,1H),2.48–2.98(m,5H), 3.13(dt,J=14.0,6.7 Hz,1H), 3.27 (ddd,J=11.6,10.5,8.0 Hz,1H), 3.48–3.64(m,2H), 3.76(s,3H), 3.78–3.89(m,2H), 4.08(s,2H), 4.37–4.50(m,1H)

IR(neat) cm$^{-1}$; 3400,2929,2870,2242,1745,1458,1439, 1401,1379,1352,1284, 1214,1138,1045,705,669

(11S,17S)-3-oxa-11-deoxy-11-(2-hydroxyethylthio)-17,20-dimethyl-13,14-didehydro-PGE$_1$ Methyl Ester $^1$H-NMR(CDCl$_3$,300 MHz) δ ppm; 0.83–0.97(m,6H), 1.08–1.81(m,15H), 2.46–3.05(m,5H), 2.91(dt,J=13.3,5.8 Hz,1H), 2.99(dt,J=13.3,5.8 Hz,1H), 3.12(ddd,J=9.9,5.4,1.8 Hz,1H), 3.54(t,J=6.8 Hz,2H), 3.59–3.68(m,1H),3.71–3.88 (m,2H), 3.75(s,3H),4.07(s,2H), 4.47(t,J=6.8 Hz,1H)

IR(neat) cm$^{-1}$; 3435,2953,2929,2870,2242,1745,1459, 1439,1401,1378,1286, 1217,1138,1045,1018,706,580

EXAMPLE 15

(11R,17S)-3-oxa-11-deoxy-11-(2-hydroxyethylthio)-17,20-dimethyl-13,14-didehydro-PGE$_1$ (Compound 82)

Following the substantially same manner as in Example 2 using (11R,17S)-3-oxa-11-deoxy-11-(2-hydroxyethylthio)-17,20-dimethyl-13,14-didehydro-PGE$_1$ methyl ester obtained in Example 14, thereby the title compound was obtained.

$^1$H-NMR(CDCl$_3$,300 MHz) δ ppm; 0.82–0.96(m,6H), 1.06–1.86(m,15H), 2.13(dd,J=18.9,11.7 Hz,1H), 2.22–2.36 (m,1H), 2.62–3.21(m,6H), 3.11(dt,J=13.8,6.7 Hz,1H), 3.28 (ddd,J=11.3,10.5,8.0 Hz,1H), 3.52–3.64(m,2H), 3.80–3.98 (m,2H), 4.08(s,2H), 4.39– 4.52(m,1H)

IR(neat) cm$^{-1}$; 3400,2928,2870,2242,1740,1459,1401, 1380,1352,1224,1131, 1045,1018,729,676

EXAMPLE 16

(11R,17R)-3-thia-11-deoxy-11-(2-hydroxyethylthio)-17,20-dimethyl-13,14-didehydro-PGE$_1$ Methyl Ester (Compound 98) and (11S,17R)-3-thia-11-deoxy-11-(2-hydroxyethylthio)-17,20-dimethyl-13,14-didehydro-PGE$_1$ methyl ester (Compound 99)

(1) Following the substantially same manner as in Example 1(1) using (17R)-3-thia-17,20-dimethyl-13,14-didehydro-PGE$_1$ methyl ester in place of (17R)-17,20-dimethyl-13,14-didehydro-PGE$_1$ methyl ester in Example 1(1), thereby (17R)-3-thia-17,20-dimethyl-13,14-didehydro-PGA$_1$ methyl ester was obtained.

$^1$H-NMR(CDCl$_3$,200 MHz) δ ppm; 0.83–0.98(m,6H), 1.12–1.98(m,16H), 1.87(d,J=5.7 Hz,1H), 2.34–2.47(m,1H), 2.67(t,J=6.9 Hz,2H), 3.24(s,2H), 3.41–3.49(m,1H), 3.75(s, 3H), 6.19(dd,J=5.7,2.3 Hz,1H), 7.48(dd,J=5.7,2.4 Hz,1H)

IR(neat) cm$^{-1}$; 3435,2952,2928,2858,2229,1734,1708, 1590,1541,1458,1436,1383, 1345,1282,1155,1132,1054, 1010,590

(2) Following the substantially same manner as in Example 1(2) using the compound obtained in the above (1), thereby the title compounds were obtained.

(11R,17R)-3-thia-11-deoxy-11-(2-hydroxyethylthio)-17,20-dimethyl-13,14-didehydro-PGE$_1$ Methyl Ester $^1$H-NMR(CDCl$_3$,200 MHz) δ ppm; 0.82–1.02(m,6H), 1.08–1.86(m,17H), 2.12(dd,J=18.9,11.6 Hz,1H), 2.17–2.37 (m,1H), 2.54–2.97(m,5H), 3.05–3.37(m,2H) 3.23(s,2H), 3.75(s,3H), 3.85(t,J=6.3 Hz,2H), 4.37–4.50(m,1H)

IR(neat) cm$^{-1}$; 3400,2952,2928,2858,2360,2235,1740, 1459,1436,1402,1379,1348, 1282,1196,1153,1046,1011, 729,593

(11S,17R)-3-thia-11-deoxy-11-(2-hydroxyethylthio)-17,20-dimethyl-13,14-didehydro-PGE$_1$ Methyl Ester $^1$H-NMR(CDCl$_3$,200 MHz) δ ppm; 0.83–0.99(m,6H), 1.10–1.85(m,17H), 2.49–2.70(m,5H), 2.91–3.03(m,2H), 3.04–3.15(m,1H), 3.23(s,2H), 3.57–3.68(m,1H), 3.75(s,3H), 3.71–3.85(m,2H), 4.40–4.54(m,1H)

IR(neat) cm$^{-1}$; 3400,2952,2928,2858,2229,1740,1638, 1459,1436,1405,1379,1283, 1222,1197,1154,1049,1010, 848,730

EXAMPLE 17

(11R,17R)-3-thia-11-deoxy-11-(2-hydroxyethylthio)-17,20-dimethyl-13,14-didehydro-PGE$_1$ (Compound 100)

Following the substantially same manner as in Example 2 using (11R,17R)-3-thia-11-deoxy-11-(2-hydroxyethylthio)-17,20-dimethyl-13,14-didehydro-PGE$_1$ methyl ester obtained in Example 16, thereby the title compound was obtained.

$^1$H-NMR(CDCl$_3$,300 MHz) δ ppm; 0.86–0.97(m,6H), 1.10–1.90(m,16H), 2.14(dd,J=18.7,11.6 Hz,1H), 2.23–2.37 (m,1H), 2.65–2.95(m,7H), 3.04–3.16(m,1H), 3.20–3.34(m, 1H), 3.23(s,2H), 3.86(t,J=6.3 Hz,2H), 4.44–4.55(m,1H)

IR(neat) cm$^{-1}$; 3399,2928,2858,2360,2229,1740,1459, 1401,1380,1348,1284,1154, 1048,1009,729,669

EXAMPLE 18

(11R,15R,17R)-3-oxa-11-deoxy-1-(2-hydroxyethylthio)-17,20-dimethyl-13,14-didehydro-PGE$_1$ Methyl Ester (Compound 72) and (11S,15R,17R)-3-oxa-11-deoxy-11-(2-hydroxyethylthio)-17,20-dimethyl-13,14-didehydro-PGE$_1$ Methyl Ester (Compound 73)

(1) Following the substantially same manner as in Example 1(1) using (15R,17R)-3-oxa-17,20-dimethyl-13,14-didehydro-PGE$_1$ methyl ester in place of (17R)-17,20-dimethyl-13,14-didehydro-PGE$_1$ methyl ester in Example 1(1), thereby (15R,17R)-3-oxa-17,20-dimethyl-13,14-didehydro-PGA$_1$ methyl ester was obtained.

$^1$H-NMR(CDCl$_3$,200 MHz) δ ppm; 0.77–1.00(m,6H), 1.06–2.16(m,15H), 2.08(d,J=5.7 Hz,1H), 2.36–2.52(m,1H), 3.37–3.66(m,3H), 3.76(s,3H), 4.09(s,2H), 4.30–4.54(m,1H), 6.19(dd,J=5.7,2.4 Hz,1H), 7.47(dd,J=5.7,2.4 Hz,1H)

IR(neat) cm$^{-1}$; 3435,2953,2929,2870,2229,1953,1755, 1708,1591,1542,1458,1438, 1378,1346,1286,1210,1139, 1042,846,809,757,706,596

(2) Following the substantially same manner as in Example 1(2) using the compound obtained in the above (1), thereby the title compounds were obtained.

(11R,15R,17R)-3-oxa-11-deoxy-11-(2-hydroxyethylthio)-17,20-dimethyl-13,14-didehydro-PGE$_1$ Methyl Ester $^1$H-NMR(CDCl$_3$,300 MHz) δ ppm; 0.83–0.96(m,6H), 1.08–1.88(m,14H), 2.03–2.97(m,7H), 2.12(dd,J=18.8,11.8 Hz,1H), 3.12(dt,J=13.8,6.5 Hz,1H), 3.26(ddd,J=11.8,10.5, 7.8 Hz,1H), 3.46–3.63(m,2H), 3.75(s,3H), 3.77–3.90(m, 2H), 4.07(s,2H), 4.36–4.52(m,1H)

IR(neat) cm$^{-1}$; 3400,2929,2870,1745,1459,1439,1401, 1380,1352,1284,1213,1138, 1045,706,596

(11S,15R,17R)-3-oxa-11-deoxy-11-(2-hydroxyethylthio)-17,20-dimethyl-13,14-didehydro-PGE$_1$ Methyl Ester $^1$H-NMR(CDCl$_3$,300 MHz) δ ppm; 0.81–0.97(m,6H), 1.06–1.81(m,15H), 2.26–2.78(m,5H), 2.85–3.05(m,2H), 3.12(ddd,J=9.8,5.5,1.9 Hz,1H), 3.54(t,J=5.8 Hz,2H), 3.63 (ddd,J=6.9,5.5,4.4 Hz,1H), 3.71–3.85(m,2H), 3.75(s,3H), 4.07(s,2H), 4.39–4.51(m,1H)

IR(neat) cm$^{-1}$; 3400,2952,2929,2870,1742,1697,1638, 1438,1401,1378,1285,1214, 1138,1045,846,769

EXAMPLE 19

(11R,15R,17R)-3-oxa-11-deoxy-11-(2-hydroxyethylthio)-17,20-dimethyl-13,14-didehydro-PGE$_1$ (Compound 76)

Following the substantially same manner as in Example 2 using (11R,15R,17R)-3-oxa-11-deoxy-11-(2-hydroxyethylthio)-17,20-dimethyl-13,14-didehydro-PGE$_1$ methyl ester obtained in Example 18, thereby the title compound was obtained.

$^1$H-NMR(CDCl$_3$,300 MHz) δ ppm; 0.78–1.00(m,6H), 1.04–1.88(m,15H), 2.13(dd,J=18.9,11.7 Hz,1H), 2.22–2.37 (m,1H), 2.52–3.01(m,3H), 3.11(dt,J=14.0,6.4 Hz,1H), 3.28 (ddd,J=11.7,10.5,7.7 Hz,1H), 3.22–3.96(m,5H), 3.85(t,J= 6.4 Hz,2H), 4.09(s,2H), 4.40–4.53(m,1H)

IR(neat) cm$^{-1}$; 3399,2929,2870,2235,1740,1460,1429, 1402,1379,1351,1283,1223, 1135,1045,1018,756,676,578

EXAMPLE 20

(11R,15R,17S)-3-oxa-11-deoxy-11-(2-hydroxyethylthio)-17,20-dimethyl-13,14-didehydro-PGE$_1$ Methyl Ester (Compound 80) and (11S,15R,17S)-3-oxa-11-deoxy-11-(2-hydroxyethylthio)-17,20-dimethyl-13,14-didehydro-PGE$_1$ Methyl Ester (Compound 81)

(1) Following the substantially same manner as in Example 1(1) using (15R,17S)-3-oxa-17,20-dimethyl-13,14-didehydro-PGE$_1$ methyl ester in place of (17R)-17,20-dimethyl-13,14-didehydro-PGE$_1$ methyl ester in Example 1(1), thereby (15R,17S)-3-oxa-17,20-dimethyl-13,14-didehydro-PGA$_1$ methyl ester was obtained.

$^1$H-NMR(CDCl$_3$,200 MHz) δ ppm; 0.82–2.10(m,21H), 2.04(d,J=5.7 Hz,1H), 2.36–2.51(m,1H), 3.42–3.64(m,3H), 3.76(s,3H), 4.09(s,2H), 4.35–4.52(m,1H), 6.18(dd,J=5.7,2.4 Hz,1H), 7.47(dd,J=5.7,2.4 Hz,1H)

IR(neat) cm$^{-1}$; 3435,2953,2929,2870,2224,1952,1755, 1708,1590,1458,1438,1379, 1346,1286,1210,1139,1061, 846,809,742,590,503

(2) Following the substantially same manner as in Example 1(2) using the compound obtained in the above (1), thereby the title compounds were obtained.

(11R,15R,17S)-3-oxa-11-deoxy-11-(2-hydroxyethylthio)-17,20-dimethyl-13,14-didehydro-PGE$_1$ Methyl Ester $^1$H-NMR(CDCl$_3$,300 MHz) δ ppm; 0.84–1.88(m,21H), 2.12(dd,J=18.8,11.8 Hz,1H), 2.14–2.36(m,1H), 2.51(t,J=6.2 Hz,1H), 2.63–2.97(m,2H), 2.68(ddd,J=11.5,10.5,1.9 Hz,1H), 2.88(dt,J=13.9,6.1 Hz,1H), 3.12(dt,J=13.9,6.5 Hz,1H), 3.26(ddd,J=11.8,10.5,7.9 Hz,1H), 3.48–3.63(m, 2H),3.75(s,3H), 3.79–3.90(m,2H), 4.07(s,2H), 4.37–4.51(m, 1H)

IR(neat) cm$^{-1}$; 3400,2953,2929,2870,2235,1745,1458, 1439,1401,1379,1284,1214, 1140,1047,706,579

(11S,15R,17S)-3-oxa-11-deoxy-11-(2-hydroxyethylthio)-17,20-dimethyl-13,14-didehydro-PGE$_1$ Methyl Ester $^1$H-NMR(CDCl$_3$,300 MHz) δ ppm; 0.84–1.81(m,21H), 2.37(t,J=6.2 Hz,1H), 2.52–2.61(m,4H), 2.86–3.05(m,2H), 3.12(ddd,J=9.7,5.4,1.9 Hz,1H), 3.54(t,J=5.9 Hz,2H) 3.63 (ddd,J=6.8,5.4,4.0 Hz,1H), 3.73–3.84(m,2H), 3.75(s,3H), 4.07(s,2H), 4.41–4.50(m,1H)

IR(neat) cm$^{-1}$; 3431,2952,2929,2870,2229,1745,1697, 1638,1456,1439,1401,1379, 1287,1217,1138,1049,846,706, 580

EXAMPLE 21

(11R,15R,17S)-3-oxa-11-deoxy-11-(2-hydroxyethylthio)-17,20-dimethyl-13,14-didehydro-PGE$_1$ (Compound 84)

Following the substantially same manner as in Example 2 using (11R,15R,17S)-3-oxa-11-deoxy-11-(2-hydroxyethylthio)-17,20-dimethyl-13,14-didehydro-PGE$_1$ methyl ester obtained in Example 20, thereby the title compound was obtained.

$^1$H-NMR(CDCl$_3$,300 MHz) δ ppm; 0.84–0.96(m,6H), 1.09–1.86(m,15H), 2.13(dd,J=18.9,11.7 Hz,1H), 2.23–2.36 (m,1H), 2.64–3.36(m,7H), 2.88(dt,J=13.9,6.4 Hz,1H), 3.54–3.64(m,2H), 3.85(t,J=6.4 Hz,2H), 4.09(s,2H), 4.42–4.52(m,1H)

IR(neat) cm$^{-1}$; 3400,2929,2870,2235,1740,1460,1402, 1379,1351,1223,1135,1050, 955,729,676

EXAMPLE 22

(11R,17S)-3-oxa-11-deoxy-11-(2-hydroxyethylthio)-20-isopropylidene-17-methyl-13,14-didehydro-PGE$_1$ Methyl Ester (Compound 89) and (11S,17S)-3-oxa-11-deoxy-11-(2-hydroxyethylthio)-20-isopropylidene-17-methyl-13,14-didehydro-PGE$_1$ Methyl Ester (Compound 90)

(1) Following the substantially same manner as in Example 1(1) using (17S)-3-oxa-20-isopropylidene-17-methyl--13,14-didehydro-PGE$_1$ methyl ester in place of (17R)-17,20-dimethyl-13,14-didehydro-PGE$_1$ methyl ester in Example 1(1), thereby (17S)-3-oxa-20-isopropylidene-17-methyl-13,14-didehydro-PGA$_1$ methyl ester was obtained.

$^1$H-NMR(CDCl$_3$,200 MHz) δ ppm; 0.82–2.10(m,16H), 1.60(s,3H), 1.68(d,J=0.9 Hz,3H), 2.15(d,J=5.7 Hz,1H), 2.35–2.50(m,1H), 3.42–3.64(m,3H), 3.76(s,3H), 4.08(s,2H), 4.37–4.51(m,1H), 5.03–5.17(m,1H), 6.19(dd,J=5.7,2.4 Hz,1H), 7.47(dd,J=5.7,2.4 Hz,1H)

IR(neat) cm$^{-1}$; 3436,2929,2866,2229,1952,1755,1711, 1591,1545,1438,1377,1346, 1287,1211,1140,1033,886,811, 706,580

(2) Following the substantially same manner as in Example 1(2) using the compound obtained in the above (1), thereby the title compounds were obtained.

(11R,17S)-3-oxa-11-deoxy-11-(2-hydroxyethylthio)-20-isopropylidene-17-methyl-13,14-didehydro-PGE$_1$ Methyl Ester $^1$H-NMR(CDC$_3$,300 MHz) δ ppm; 0.84–2.06(m,16H), 1.61(s,3H), 1.68(d,J=0.9 Hz,3H), 2.13(dd,J=18.8,11.7 Hz,1H), 2.20–2.36(m,1H), 2.46(t,J=6.4 Hz,1H), 2.62–2.98 (m,3H), 2.87(dt,J=13.8,6.1 Hz,1H), 3.12(dt,J=13.8,6.5 Hz,1H), 3.26(ddd,J=11.7,10.5,7.9 Hz,1H), 3.46–3.64(m, 2H),3.75(s,3H), 3.78–3.90(m,2H), 4.07(s,2H), 4.37–4.52(m, 1H), 5.05–5.14(m,1H)

IR(neat) cm$^{-1}$; 3400,2928,2869,2229,1745,1438,1401, 1378,1284,1213,1138,1045, 705,580

(11S,17S)-3-oxa-11-deoxy-11-(2-hydroxyethylthio)-20-isopropylidene-17-methyl-13,14-didehydro-PGE$_1$ Methyl Ester $^1$H-NMR(CDCl$_3$,300 MHz) δ ppm; 0.85–2.08(m,16H), 1.61(s,3H), 1.68(d,J=1.1 Hz,3H), 2.40–2.68(m,4H), 2.78(d, J=4.8 Hz,1H), 2.86–3.05(m,2H), 3.11(ddd,J=9.9,5.3,1.7 Hz,1H), 3.53(t,J=5.9 Hz,2H), 3.63(ddd,J=6.8,5.3,3.8 Hz,1H), 3.70–3.86(m,2H), 3.75(s,3H), 4.07(s,2H), 4.38–4.53(m,1H), 5.04–5.15(m,1H)

IR(neat) cm$^{-1}$; 3431,2924,2869,2235,1745,1697,1641, 1439,1401,1376,1287,1214, 1138,1045,706,580

EXAMPLE 23

(11R,17S)-3-oxa-11-deoxy-11-(2-hydroxyethylthio)-20-isopropylidene-17-methyl-13,14-didehydro-PGE$_1$ (Compound 91)

Following the substantially same manner as in Example 2 using (11R,17S)-3-oxa-11-deoxy-11-(2-hydroxyethylthio)-20-isopropylidene-17-methyl-13,14-didehydro-PGE$_1$ methyl ester obtained in Example 22, thereby the title compound was obtained.

$^1$H-NMR(CDCl$_3$,300 MHz) δ ppm; 0.84–2.09(m,16H), 1.61(s,3H), 1.68(s,3H), 2.13(dd,J=18.9,11.7 Hz,1H), 2.22–2.37(m,1H), 2.52–3.20(m,6H), 3.11(dt,J=13.8,6.5 Hz,1H), 3.28(ddd,J=11.7,10.5,7.9 Hz,1H), 3.52–3.67(m, 2H),3.74–3.93(m,2H), 4.08(s,2H), 4.40–4.53(m,1H), 5.04–5.15(m,1H)

IR(neat) cm$^{-1}$; 3400,2928,2235,1740,1434,1401,1378, 1351,1227,1132,1045,676

EXAMPLE 24

(11R,17R)-3-oxa-11-deoxy-11-(2-hydroxyethylthio)-20-isopropylidene-17-methyl-13,14-didehydro-PGE$_1$ Methyl Ester (Compound 92) and (11S,17R)-3-oxa-11-deoxy-11-(2-hydroxyethylthio)-20-isopropylidene-17-methyl-13,14-didehydro-PGE$_1$ Methyl Ester (Compound 93)

(1) Following the substantially same manner as in Example 1(1) using (17R)-3-oxa-20-isopropylidene-17-methyl-13,14-didehydro-PGE$_1$ methyl ester in place of (17R)-17,20-dimethyl-13,14-didehydro-PGE$_1$ methyl ester in Example 1(1), thereby (17R)-3-oxa-20-isopropylidene-17-methyl-13,14-didehydro-PGA$_1$ methyl ester was obtained.

$^1$H-NMR(CDCl$_3$, 300 MHz) δ ppm; 0.90–0.97(m,3H), 1.10–2.05(m,13H), 1.60(s,3H), 1.68(s,3H), 2.08(d,J=5.8 Hz,1H), 2.38–2.50(m,1H), 3.43–3.63(m,3H), 3.76(s,3H), 4.09(s,2H), 4.39–4.50(m,1H), 5.04–5.14(m,1H), 6.16–6.21 (m,1H), 7.43–7.50(m,1H)

IR(neat) cm$^{-1}$; 3435,2929,2866,2229,1755,1711,1591, 1545,1438,1377,1346,1287, 1210,1139,1059,887,812,706, 579,429

(2) Following the substantially same manner as in Example 1(2) using the compound obtained in the above (1), thereby the title compounds were obtained.

(11R,17R)-3-oxa-11-deoxy-1-(2-hydroxyethylthio)-20-isopropylidene-17-methyl-13,14-didehydro-PGE$_1$ Methyl Ester $^1$H-NMR(CDCl$_3$,300 MHz) δ ppm; 0.90–0.97(m,3H), 1.10–2.03(m,15H), 1.60(s,3H), 1.68(s,3H), 2.12(dd,J=18.8, 11.7 Hz,1H), 2.27–2.36(m,1H), 2.62–2.93(m,2H), 2.87(dt, J=13.8,6.1 Hz,1H), 3.12(dt,J=13.8,6.4 Hz,1H), 3.27(ddd,J= 11.7,10.5,7.8 Hz,1H), 3.48–3.58(m,2H), 3.75(s,3H), 3.80–3.87(m,2H), 4.07(s,2H), 4.39–4.49(m,1H), 5.05–5.13 (m,1H)

IR(neat) cm$^{-1}$; 3435,2928,2869,2235,1745,1439,1401, 1378,1284,1213,1139,1046, 705,580

(11S,17R)-3-oxa-11-deoxy-11-(2-hydroxyethylthio)-
20-isopropylidene-17-methyl-13,14-didehydro-PGE$_1$
Methyl Ester $^1$H-NMR(CDCl$_3$,300 MHz) δ ppm; 0.94(d,J=6.5 Hz,3H), 1.12–2.06(m,15H), 1.60(s,3H), 1.68(s,3H), 2.47–2.66(m, 3H), 2.85–3.05(m,2H), 3,07–3.16(m,1H), 3.48–3.57(m,2H), 3.59–3.67(m,1H), 3.69–3.83(m,2H), 3.75(s,3H), 4.07(s,2H), 4.41–4.48(m,1H), 5.05–5.13(m,1H)

IR(neat) cm$^{-1}$; 3400,2928,2869,1742,1438,1401,1377, 1284,1213,1138,1046,846, 741,579

EXAMPLE 25

(11R,17R)-3-oxa-11-deoxy-11-(2-hydroxyethylthio)-
20-isopropylidene-17-methyl-13,14-didehydro-PGE$_1$
(Compound 94)

Following the substantially same manner as in Example 2 using (11R,17R)-3-oxa-11-deoxy-11-(2-hydroxyethylthio)-20-isopropylidene-17-methyl-13,14-didehydro-PGE$_1$ methyl ester obtained in Example 24, thereby the title compound was obtained.

$^1$H-NMR(CDCl$_3$,300 MHz) δ ppm; 0.95(d,J=6.7 Hz,3H), 1.12–2.06(m,16H), 1.61(s,3H), 1.68(d,J=1.1 Hz,3H), 2.13 (dd,J=19.0,11.7 Hz,1H), 2.22– 2.36(m,1H), 2.62–2.86(m, 2H), 2.88(dt,J=13.8,6.2 Hz,1H), 3.11(dt,J=13.8,6.6 Hz,1H), 3.27(ddd,J=11.7,10.3,8.0 Hz,1H), 3.54–3.64(m,2H), 3.81–3.88(m,2H), 4.09(s,2H), 4.39–4.51(m,1H),5.04–5.14 (m,1H)

IR(neat) cm$^{-1}$; 3400,2929,2235,1740,1434,1402,1378, 1351,1223,1135,1049,676

EXAMPLE 26

(11R)-3-oxa-11-deoxy-11-(2-hydroxyethylthio)-13,
14-didehydro-PGE$_1$ Methyl Ester (Compound 95)
and (11S)-3-oxa-11-deoxy-11-(2-hydroxyethylthio)-
13,14-didehydro-PGE$_1$ Methyl Ester (Compound
96)

(1) Following the substantially same manner as in Example 1(1) using 3-oxa-13,14-didehydro-PGE$_1$ methyl ester in place of (17R)-17,20-dimethyl-13,14-didehydro-PGE$_1$ methyl ester in Example 1(1), thereby 3-oxa-13,14-didehydro-PGA$_1$ methyl ester was obtained.

$^1$H-NMR(CDCl$_3$, 300 MHz) δ ppm; 0.86–0.93(m,3H), 1.22–1.80(m,14H), 2.12(d,J=5.8 Hz,1H), 2.40–2.47(m,1H), 3.44–3.59(m,3H), 3.76(s,3H), 4.08(s,2H), 4.30–4.40(m,1H), 6.18(dd,J=5.7,2.4 Hz,1H), 7.47(dd,J=5.7,2.5 Hz,1H)

IR(neat) cm$^{-1}$; 3436,2934,2860,2235,1954,1755,1708, 1591,1545,1438,1399,1378, 1345,1287,1211,1139,1028, 888,847,811,773,706,580

(2) Following the substantially same manner as in Example 1(2) using the compound obtained in the above (1), thereby the title compounds were obtained.

(11R)-3-oxa-11-deoxy-11-(2-hydroxyethylthio)-13,
14-didehydro-PGE$_1$ Methyl Ester $^1$H-NMR(CDCl$_3$,300 MHz) δ ppm; 0.86–0.94(m,3H), 1.22–1.88(m,16H), 2.12(dd,J=18.7,11.7 Hz,1H), 2.22–2.37 (m,1H), 2.63–2.93(m,3H), 3.12(dt,J=14.0,6.4 Hz,1H), 3.27 (ddd,J=11.7,10.8,8.1 Hz,1H), 3.48–3.60(m,2H), 3.76(s,3H), 3.84(t,J=6.4 Hz,2H), 4.08(s,2H), 4.30–4.42(m,1H)

IR(neat) cm$^{-1}$; 3435,2933,2860,2229,1745,1439,1401, 1348,1283,1214,1138,1045, 707,580

(11S)-3-oxa-11-deoxy-11-(2-hydroxyethylthio)-13,
14-didehydro-PGE$_1$ Methyl Ester $^1$H-NMR(CDCl$_3$,300 MHz) δ ppm; 0.86–0.94(m,3H), 1.20–1.80(m,16H), 2.52–2.66(m,3H), 2.86–3.05(m,2H), 3,08–3.16(m,1H), 3.48–3.58(m,2H), 3.60–3.67(m,1H), 3.72–3.83(m,2H), 3.76(s,3H), 4.08(s,2H), 4.34–4.42(m,1H)

IR(neat) cm$^{-1}$; 3400,2930,2862,2229,1740,1439,1401, 1284,1218,1138,1046,1014, 847,706,580

EXAMPLE 27

(11R)-3-oxa-11-deoxy-11-(2-hydroxyethylthio)-13,
14-didehydro-PGE$_1$ (Compound 97)

Following the substantially same manner as in Example 2 using (11R)-3-oxa-11-deoxy-11-(2-hydroxyethylthio)-13, 14-didehydro-PGE$_1$ methyl ester obtained in Example 26, thereby the title compound was obtained.

$^1$H-NMR(CDCl$_3$,300 MHz) δ ppm; 0.85–0.95(m,3H), 1.22–1.84(m,18H), 2.13(dd,J=18.8,11.7 Hz,1H), 2.23–2.36 (m,1H), 2.69(ddd,J=13.5,10.6,1.9 Hz,1H), 2.80(ddd,J=18.8, 7.9,1.4 Hz,1H), 2.88(dt,J=13.9,6.3 Hz,1H), 3.11(dt,J=13.9, 6.3 Hz,1H), 3.28(ddd,J=11.7,10.6,7.9 Hz,1H), 3.54–3.64(m, 2H), 3.85(t,J=6.3 Hz,1H), 4.09(s,2H), 4.41(dt,J=1.9,6.6 Hz,1H)

IR(neat) cm$^{-1}$; 3400,2933,2860,2235,1740,1402,1347, 1223,1132,1046,729,676

EXAMPLE 28

(2E,11R,17R)-11-deoxy-17,20-dimethyl-11-(2-
hydroxyethylthio)-2,3,13,14-tetradehydro-PGE$_1$
Methyl Ester (Compound 44) and (2E,11S,17R)-11-
deoxy-17,20-dimethyl-11-(2-hydroxyethylthio)-2,3,
13,14-tetradehydro-PGE$_1$ Methyl Ester (Compound
46)

(1) Following the substantially same manner as in Example 1(1) using (2E,17R)-17,20-dimethyl-2,3,13,14-tetradehydro-PGE$_1$ methyl ester in place of (17R)-17,20-dimethyl-13,14-didehydro-PGE$_1$ methyl ester in Example 1(1), thereby (2E,17R)-17,20-dimethyl-2,3,13,14-tetradehydro-PGA$_1$ methyl ester was obtained.

$^1$H-NMR(CDCl$_3$,300 MHz) δ ppm; 0.81–0.99(m,6H), 1.06–2.08(m,16H), 2.13–2.48(m,3H), 3.38–3.48(m,1H), 3.74(s,3H), 4.37–4.56(m,1H), 5.84(dt,J=15.6,1.4 Hz,1H), 6.19(dd,J=5.6,2.2 Hz,1H), 6.98(dt,J=15.6,7.0 Hz,1H), 7.48 (dd,J=5.6,2.4 Hz,1H)

IR(neat) cm$^{-1}$: 3441,2952,2929,2858,2224,1718,1697, 1654,1591,1457,1436,1379, 1342,1273,1201,1177,1155, 1110,1038,981,855

(2) Following the substantially same manner as in Example 1(2) using the compound obtained in the above (1), thereby the title compounds were obtained.

(2E,11R,17R)-11-deoxy-17,20-dimethyl-11-(2-
hydroxyethylthio)-2,3,13,14-tetradehydro-PGE$_1$
Methyl Ester $^1$H-NMR(CDCl$_3$,300 MHz) δ ppm; 0.83–0.97(m,6H), 1.06–1.85(m,15H), 2.04–2.97(m,7H), 2.11(dd,J=18.8,11.7 Hz,1H), 2.87(dt,J=13.9,6.2 Hz,1H), 3.14(dt,J=13.9,6.8 Hz,1H), 3.28(ddd,J=11.7,10.4,7.9 Hz,1H), 3.73(s,3H), 3.79–3.91(m,2H), 4.45(ddd,J=8.0,5.9,1.8 Hz,1H), 5.83(dt, J=15.6,1.5 Hz,1H), 6.96(dd,J=15.6,7.0 Hz,1H)

IR(neat) cm$^{-1}$: 3416,2952,2929,2859,2229,1740,1723, 1653,1457,1436,1401,1376, 1311,1278,1202,1174,1158, 1045,984,844

(2E,11S,17R)-11-deoxy-17,20-dimethyl-11-(2-
hydroxyethylthio)-2,3,13,14-tetradehydro-PGE$_1$
Methyl Ester $^1$H-NMR(CDCl$_3$,300 MHz) δ ppm; 0.84–0.99(m,6H), 1.08–1.83(m,15H), 2.15–3.13(m,9H), 3.08(ddd,J=10.2,5.4, 1.6 Hz,1H), 3.62(ddd,J=6.9,5.4,3.7 Hz,1H), 3.66–3.90(m, 2H), 3.73(s,3H),4.40–4.53(m,1H), 5.83(dt,J=15.7,1.5 Hz,1H), 6.96(dt,J=15.7,7.0 Hz,1H)

IR(neat) cm$^{-1}$: 3432,2952,2929,2862,2229,1734,1709, 1654,1460,1436,1401,1376, 1314,1278,1201,1163,1045, 981,847

EXAMPLE 29

(2E,11R,17R)-11-deoxy-17,20-dimethyl-11-(2-hydroxyethylthio)-2,3,13,14-tetradehydro-PGE$_1$ (Compound 45)

Following the substantially same manner as in Example 2 using (2E,11R,17R)-11-deoxy-17,20-dimethyl-11-(2-hydroxyethylthio)-2,3,13,14-tetradehydro-PGE$_1$ methyl ester obtained in Example 28, thereby the title compound was obtained.

$^1$H-NMR(CDCl$_3$,300 MHz) δ ppm; 0.83–0.96(m,6H), 1.06–1.84(m,18H), 2.11(dd,J=19.0,11.7 Hz,1H), 2.18–2.33 (m,3H), 2.60–2.96(m,2H), 2.87(dt,J=14.0,6.4 Hz,1H), 3.15 (dt,J=14.0,6.2 Hz,1H), 3.28(ddd,J=11.7,10.4,7.8 Hz,1H), 3.79–3.89(m,2H), 4.38–4.49(m,1H), 5.84(dt,J=15.7,1.6 Hz,1H), 7.06(dt,J=15.7,7.0 Hz,1H)

IR(neat) cm$^{-1}$: 3368,2929,2857,1743,1697,1653,1460, 1384,1284,1155,1048

EXAMPLE 30

(2E,11S,17R)-11-deoxy-17,20-dimethyl-11-(2-hydroxyethylthio)-2,3,13,14-tetradehydro-PGE$_1$ (Compound 47)

Following the substantially same manner as in Example 2 using (2E,11S,17R)-11-deoxy-17,20-dimethyl-11-(2-hydroxyethylthio)-2,3,13,14-tetradehydro-PGE$_1$ methyl ester obtained in Example 28, thereby the title compound was obtained.

$^1$H-NMR(CDCl$_3$,300 MHz) δ ppm; 0.83–0.96(m,6H), 1.08–1.82(m,18H), 2.17–2.34(m,2H), 2.46–2.67(m,2H), 2.86–3.12(m,3H), 3.58–3.66(m,1H), 3.73–3.88(m,3H), 4.45–4.55(m,1H), 5.79–5.89(m,1H), 7.05(dt,J=15.7,7.1 Hz,1H)

IR(neat) cm$^{-1}$: 3390,2929,2862,1739,1697,1653,1462, 1404,1284,1163,1048,984

EXAMPLE 31

(11R,16S)-3-oxa-11-deoxy-11-(2-hydroxyethylthio)-16,20-dimethyl-13,14-didehydro-PGE$_1$ Methyl Ester (Compound 101) and (11S,16S)-3-oxa-11-deoxy-11-(2-hydroxyethylthio)-16,20-dimethyl-13,14-didehydro-PGE$_1$ Methyl Ester (Compound 102)

(1) Following the substantially same manner as in Example 1(1) using (16S)-3-oxa-16,20-dimethyl-13,14-didehydro-PGE$_1$ methyl ester in place of (17R)-17,20-dimethyl-13,14-didehydro-PGE$_1$ methyl ester in Example 1(1), thereby (16S)-3-oxa-16,20-dimethyl-13,14-didehydro-PGA$_1$ Methyl Ester was obtained.

$^1$H-NMR(CDCl$_3$,200 MHz) δ ppm; 0.89(t,J=6.6 Hz,3H), 0.97(d,J=6.6 Hz,3H), 1.04–2.06(m,15H), 2.10(d,J=5.9 Hz,1H), 2.30–2.48(m,1H), 3.43–3.64(m,3H), 3.76(s,3H), 4.08(s,2H), 4.22–4.34(m,1H), 6.19(dd,J=5.7,2.2 Hz,1H), 7.48(dd,J=5.7,2.4 Hz,1H)

IR(neat) cm$^{-1}$: 3467,2929,2859,2212,1752,1708,1591, 1459,1438,1383,1346,1285, 1211,1139,1026,895,810,768, 605

(2) Following the substantially same manner as in Example 1(2) using the compound obtained in the above (1), thereby the title compounds were obtained.

(11R,16S)-3-oxa-11-deoxy-11-(2-hydroxyethylthio)-16,20-dimethyl-13,14-didehydro-PGE$_1$ Methyl Ester $^1$H-NMR(CDCl$_3$,300 MHz) δ ppm; 0.89(t,J=6.8 Hz,3H), 1.00(d,J=6.7 Hz,3H), 1.16–1.76(m,15H), 2.13(dd,J=18.8, 11.7 Hz,1H), 2.24–2.36(m,1H), 2.39–2.52(m,1H), 2.61–2.94(m,4H), 3.11(dt,J=14.0,6.6 Hz,1H), 3.18–3.36(m, 1H), 3.46–3.58(m,2H), 3.76(s,3H), 3.77–3.89(m,2H), 4.07 (s,2H), 4.24–4.32(m,1H)

IR(neat) cm$^{-1}$: 3435,2928,2859,1745,1459,1439,1401, 1380,1352,1283,1214,1140, 1044,1016,726,580

(11S,16S)-3-oxa-11-deoxy-11-(2-hydroxyethylthio)-16,20-dimethyl-13,14-didehydro-PGE$_1$ Methyl Ester $^1$H-NMR(CDCl$_3$,300 MHz) δ ppm; 0.89(t,J=6.8 Hz,3H), 1.00(d,J=6.7 Hz,3H), 1.12–1.80(m,15H), 2.36(br s,1H), 2.47–2.67(m,4H), 2.84–3.03(m,2H), 3.13(ddd,J=9.6,5.6,1.9 Hz,1H), 3.47–3.58(m,2H), 3.60–3.68(m,1H), 3.70–3.84(m, 2H), 3.75(s,3H), 4.07(s,2H), 4.28–4.34(m,1H)

IR(neat) cm$^{-1}$: 3435,2928,2859,1742,1638,1459,1438, 1401,1378,1284,1215,1139, 1045,1016,706,579

EXAMPLE 32

(11R,16S)-3-oxa-11-deoxy-11-(2-hydroxyethylthio)-16,20-dimethyl-13,14-didehydro-PGE$_1$ (Compound 103)

Following the substantially same manner as in Example 2 using (11R,16S)-3-oxa-11-deoxy-11-(2-hydroxyethylthio)-16,20-dimethyl-13,14-didehydro-PGE$_1$ methyl ester obtained in Example 31, thereby the title compound was obtained.

$^1$H-NMR(CDCl$_3$,300 MHz) δ ppm; 0.89(t,J=6.7 Hz,3H), 1.00(d,J=6.7 Hz,3H), 1.10–1.88(m,15H), 2.13(dd,J=18.9, 11.6 Hz,1H), 2.22–2.39(m,1H), 2.52–2.61(m,1H), 2.65–3.01 (m,4H), 3.10(dt,J=13.8,6.5 Hz,1H), 3.22–4.22(m,1H), 3.29 (ddd,J=11.6,10.7,8.1 Hz,1H), 3.51–3.63(m,2H), 3.84(t,J= 6.4 Hz,2H), 4.09(s,2H),4.26–4.36(m,1H)

IR(neat) cm$^{-1}$: 3400,2929,2859,2235,1740,1460,1402, 1351,1224,1134,1044,1014, 728,676

EXAMPLE 33

(11R,16R)-3-oxa-11-deoxy-11-(2-hydroxyethylthio)-16,20-dimethyl-13,14-didehydro-PGE$_1$ Methyl Ester (Compound 104) and (11S,16R)-3-oxa-11-deoxy-11-(2-hydroxyethylthio)-16,20-dimethyl-13,14-didehydro-PGE$_1$ Methyl Ester (Compound 105)

(1) Following the substantially same manner as in Example 1(1) using (16R)-3-oxa-16,20-dimethyl-13,14-didehydro-PGE$_1$ methyl ester in place of (17R)-17,20-dimethyl-13,14-didehydro-PGE$_1$ methyl ester in Example 1(1), thereby (16R)-3-oxa-16,20-dimethyl-13,14-didehydro-PGA$_1$ methyl ester was obtained.

$^1$H-NMR(CDCl$_3$+D$_2$O,300 MHz) δ ppm; 0.89(t,J=6.8 Hz,3H), 0.96(d,J=6.8 Hz,3H), 1.05–2.02(m,15H), 2.38–2.49 (m,1H), 3.45–3.59(m,3H), 3.76(s,3H), 4.08(s,2H), 4.24(dd, J=4.9,1.9 Hz,1H), 6.19(dd,J=5.7,2.4 Hz,1H), 7.48(dd,J=5.7, 2.4 Hz,1H)

IR(neat) cm$^{-1}$: 3468,2930,2859,2211,1752,1708,1592, 1545,1459,1439,1380,1346, 1283,1212,1139,1027,887,811, 772,706,580

(2) Following the substantially same manner as in Example 1(2) using the compound obtained in the above (1), thereby the title compounds were obtained.

(11R,16R)-3-oxa-11-deoxy-11-(2-hydroxyethylthio)-16,20-dimethyl-13,14-didehydro-PGE$_1$ Methyl Ester $^1$H-NMR(CDCl$_3$+D$_2$O,300 MHz) δ ppm; 0.83–1.03(m, 3H), 0.99(d,J=6.7 Hz,3H), 1.08–1.90(m,15H), 2.13(dd,J= 18.8,11.8 Hz,1H), 2.23–2.38(m,1H), 2.63–2.97(m,3H), 3.12 (dt,J=13.8,6.5 Hz,1H), 3.28(ddd,J=11.8,10.5,7.8,1H), 3.46–3.65(m,2H), 3.76(s,3H), 3.83(t,J=6.5 Hz,2H), 4.07(s, 2H), 4.20–4.30(m,1H)

IR(neat) cm$^{-1}$: 3435,2929,2859,2235,1745,1459,1439, 1401,1378,1283,1214,1139, 1045,726,580,428

(11S,16R)-3-oxa-11-deoxy-11-(2-hydroxyethylthio)-16,20-dimethyl-13,14-didehydro-PGE$_1$ Methyl Ester $^1$H-NMR(CDCl$_3$,300 MHz) δ ppm; 0.83–1.03(m,3H), 1.00(d,J=6.7 Hz,3H), 1.12–1.82(m,15H), 2.00–2.44(m,2H), 2.47–2.78(m,3H), 2.84–3.04(m,2H), 3.13(ddd,J=9.8,5.4,1.9 Hz,1H), 3.53(t,J=5.8 Hz,2H), 3.59–3.68(m,1H), 3.71–3.87 (m,2H), 3.75(s,3H), 4.07(s,2H),4.20–4.34(m,1H)

IR(neat) cm$^{-1}$: 3432,2929,2859,2235,1745,1697,1637, 1456,1439,1401,1376,1284, 1217,1138,1046,1015,888,706, 580

EXAMPLE 34

(11R,16R)-3-oxa-11-deoxy-11-(2-hydroxyethylthio)-16,20-dimethyl-13,14-didehydro-PGE$_1$ (Compound 106)

Following the substantially same manner as in Example 2 using (11R,16R)-3-oxa-11-deoxy-11-(2-hydroxyethylthio)-16,20-dimethyl-13,14-didehydro-PGE$_1$ methyl ester obtained in Example 33, thereby the title compound was obtained.

$^1$H-NMR(CDCl$_3$+D$_2$O,300 MHz) δ ppm; 0.83–1.05(m, 6H) ,1.10–1.90(m,17H), 2.13(dd,J=18.8,11.8 Hz,1H), 2.23–2.37(m,1H), 2.52–3.03(m,2H), 2.87(dt,J=14.0,6.1 Hz,1H), 3.11(dt,J=14.0,6.5 Hz,1H), 3.28(ddd,J=11.8,10.3, 7.9 Hz,1H), 3.40–4.00(m,3H), 3.57(t,J=5.8 Hz,2H), 4,09(s, 2H), 4.23–4.33(m,1H)

IR(neat) cm$^{-1}$: 3426,2929,2859,1740,1459,1401,1379, 1348,1224,1135,1045,1013, 940,727,676

EXAMPLE 35

(11R,15RS)-3-oxa-11-deoxy-11-(2-hydroxyethylthio)-16,16-dimethyl-13,14-didehydro-PGE$_1$ Methyl Ester (Compound 107) and (11S, 15RS)-3-oxa-11-deoxy-11-(2-hydroxyethylthio)-16, 16-dimethyl-13,14-didehydro-PGE$_1$ Methyl Ester (Compound 108)

(1) Following the substantially same manner as in Example 1(1) using (15RS)-3-oxa-16,16-dimethyl-13,14-didehydro-PGE$_1$ methyl ester in place of (17R)-17,20-dimethyl-13,14-didehydro-PGE$_1$ methyl ester in Example 1(1), thereby (15RS)-3-oxa-16,16-dimethyl-13,14-didehydro-PGA$_1$ methyl ester was obtained.

$^1$H-NMR(CDCl$_3$,300 MHz) δ ppm; 0.86–0.99(m,9H), 1.18–2.02(m,13H), 2.38–2.47(m,1H), 3.46– 3.60(m,3H), 3.76(s,3H), 4.04–4.15(m,1H), 4.08(s,2H), 6.19(dd,J=5.7,2.4 Hz,1H), 7.48(dd,J=5.7,2.3 Hz,1H)

IR(neat) cm$^{-1}$: 3468,2955,2933,2870,2207,1752,1708, 1591,1542,1458,1438,1384, 1345,1283,1212,1139,1033, 811,706,579

(2) Following the substantially same manner as in Example 1(2) using the compound obtained in the above (1), thereby the title compounds were obtained.

(11R,15RS)-3-oxa-11-deoxy-11-(2-hydroxyethylthio)-16,16-dimethyl-13,14-didehydro-PGE$_1$ Methyl Ester $^1$H-NMR(CDCl$_3$,300 MHz) δ ppm; 0.86–0.99(m,9H), 1.16–3.36(m,20H), 2.14(dd,J=18.7,11.7 Hz,1H), 3.48–3.58 (m,2H), 3.76(s,3H), 3.78–3.91(m,2H), 4.04–4.15(m,1H), 4.07(s,2H)

IR(neat) cm$^{-1}$: 3435,2955,2932,2870,1745,1439,1384, 1283,1214,1139,1039,767, 729,579

(11S,15RS)-3-oxa-11-deoxy-11-(2-hydroxyethylthio)-16, 16-dimethyl-13,14-didehydro-PGE$_1$ methyl ester $^1$H-NMR (CDCl$_3$,300 MHz) δ ppm; 0.86–0.98(m,9H), 1.16–1.78(m, 13H), 2.–14 2.41(m,1H), 2.43–2.60(m,4H), 2.82–3.02(m, 2H), 3.11–3.18(m,1H), 3.48–3.84(m,4H), 3.76(s,3H), 4.03–4.15(m,1H), 4.07(s,2H)

IR(neat) cm$^{-1}$: 3435,2955,2932,2870,2229,1742,1638, 1439,1384,1284,1215,1139, 1039,706,579

EXAMPLE 36

(11R,15RS)-3-oxa-11-deoxy-11-(2-hydroxyethylthio)-16,16-dimethyl-13,14-didehydro-PGE$_1$ (Compound 109)

Following the substantially same manner as in Example 2 using (11R,15RS)-3-oxa-11-deoxy-11-(2-hydroxyethylthio)-16,16-dimethyl-13,14-didehydro-PGE$_1$ methyl ester obtained in Example 35, thereby the title compound was obtained.

$^1$H-NMR(CDCl$_3$,300 MHz) δ ppm; 0.85–1.02(m,9H), 1.14–1.86(m,12H), 2.14(dd,J=18.9,11.4 Hz,1H), 2.24–3.36 (m,9H), 3.54–3.66(m,2H), 3.79–3.88(m,2H), 4.06–4.17(m, 1H), 4.09(s,2H)

IR(neat) cm$^{-1}$: 3431,2933,2870,2229,1740,1468,1432, 1385,1364,1281,1223,1135, 1024,761,676

EXAMPLE 37

(11R,17R)-4-oxa-11-deoxy-11-(2-hydroxyethylthio)-17,20-dimethyl-13,14-didehydro-PGE$_1$ Methyl Ester (Compound 85) and (11S,17R)-4-oxa-11-deoxy-11-(2-hydroxyethylthio)-17,20-dimethyl-13,14-didehydro-PGE$_1$ Methyl Ester (Compound 86)

(1) Following the substantially same manner as in Example 1(1) using (17R)-4-oxa-17,20-dimethyl-13,14-didehydro-PGE$_1$ methyl ester in place of (17R)-17,20-dimethyl-13,14-didehydro-PGE$_1$ methyl ester in Example 1(1), thereby (17R)-4-oxa-17,20-dimethyl-13,14-didehydro-PGA$_1$ methyl ester was obtained.

$^1$H-NMR(CDCl$_3$,200 MHz) δ ppm; 0.81–1.05(m,3H), 0.92(d,J=6.6 Hz,3H), 1.07–2.04(m,14H), 2.42(ddd,J=9.2, 4.6,3.3 Hz,1H), 2.58(t,J=6.3 Hz,2H), 3.39– 3.60(m,3H), 3.61–3.83(m,2H), 3.70(s,3H), 4.28–4.54(m,1H), 6.18(dd,J= 5.7,2.2 Hz,1H), 7.47(dd,J=5.7,2.4 Hz,1H)

IR(neat) cm$^{-1}$: 3436,2955,2930,2871,2214,1740,1708, 1457,1438,1376,1326,1262, 1198,1179,1116,1068,1028, 848

(2) Following the substantially same manner as in Example 1(2) using the compound obtained in the above (1), thereby the title compounds were obtained.

(11R,17R)-4-oxa-11-deoxy-11-(2-hydroxyethylthio)-17,20-dimethyl-13,14-didehydro-PGE$_1$ Methyl Ester $^1$H-NMR(CDCl$_3$,200 MHz) δ ppm; 0.75–1.02(m,3H), 0.93(d,J=6.6 Hz,3H), 1.04–3.00(m,19H), 2.12(dd,J=18.9, 11.6 Hz,1H), 2.57(t,J=6.4 Hz,2H), 3.15(dt,J=20.4,6.3 Hz,1H), 3.28(ddd,J=11.6,10.4,7.8 Hz,1H), 3.36–3.55(m, 2H), 3.68(t,J=6.4 Hz,2H), 3.70(s,3H), 3.85(t,J=6.3 Hz,2H), 4.34–4.53(m,1H)

IR(neat) cm$^{-1}$: 3432,2955,2929,2871,2236,1746,1740, 1456,1440,1402,1380,1326, 1282,1197,1179,1154,1116, 1062,849,590

(11S,17R)-4-oxa-11-deoxy-11-(2-hydroxyethylthio)-17,20-dimethyl-13,14-didehydro-PGE$_1$ Methyl Ester $^1$H-NMR(CDCl$_3$,200 MHz) δ ppm; 0.81–1.04(m,3H), 0.93(d,J=6.6 Hz,3H), 1.08–3.18(m,20H), 2.58(t,J=6.4 Hz,2H), 3.11(ddd,J=9.8,5.3,1.8 Hz,1H), 3.–14 3.85(m,5H), 3.69(t,J=6.4 Hz,2H), 3.70(s,3H), 4.36–4.56(m,1H)

IR(neat) cm$^{-1}$: 3432,2953,2929,2871,2236,1740,1456, 1439,1402,1376,1338,1284, 1198,1177,1116,1062,849,593

EXAMPLE 38

(11R,17R)-4-oxa-11-deoxy-11-(2-hydroxyethylthio)-17,20-dimethyl-13,14-didehydro-PGE$_1$ (Compound 87)

Following the substantially same manner as in Example 2 using (11R,17R)-4-oxa-11-deoxy-11-(2-hydroxyethylthio)-17,20-dimethyl-13,14-didehydro-PGE$_1$ methyl ester obtained in Example 37, thereby the title compound was obtained.

$^1$H-NMR(CDCl$_3$,200 MHz) δ ppm; 0.78–1.00(m,3H), 0.93(d,J=6.6 Hz,3H), 1.06–2.00(m,14H), 2.12(dd,J=18.9, 11.5 Hz,1H), 2.23–4.63(m,9H), 2.58(t,J=5.8 Hz,2H), 2.79 (ddd,J=18.9,7.8,1.6 Hz,1H), 2.87(dt,J=14.0,6.2 Hz,1H), 3.12(dt,J=14.0,6.4 Hz,1H), 3.30(ddd,J=11.5,10.4,7.8 Hz,1H), 3.70(t,J=5.8 Hz,2H)

IR(neat) cm$^{-1}$: 3400,2956,2930,2870,2236,1746,1740, 1456,1402,1380,1326,1283, 1196,1158,1116,1056,935,844, 594

EXAMPLE 39

(11R,17R)-3-oxa-11-deoxy-11-(2-hydroxyethylsulfinyl)-17,20-dimethyl-13,14-didehydro-PGE$_1$ Methyl Ester (Compound 75)

To a methanol solution (2.2 ml) of (11R,17R)-3-oxa-11-deoxy-11-(2-hydroxyethylthio)-17,20-dimethyl-13,14-didehydro-PGE$_1$ methyl ester obtained in Example 12 (40 mg) was added an aqueous solution (0.9 ml) of sodium periodate (71 mg) at room temperature, followed by stirring at the same temperature for 1.5 hours. The reaction solution was added to a mixture of ethyl acetate and a saturated aqueous sodium chloride solution and, after separation of the organic layer, an aqueous layer was extracted with ethyl acetate, and the organic layers were combined, washed with a saturated aqueous sodium chloride solution and dried over anhydrous magnesium sulfate. Filtration and concentration gave a crude product, which was then purified by a silica gel column chromatography (developing solvent; ethyl acetate) to give the title compound (39 mg).

$^1$H-NMR(CDCl$_3$,300 MHz) δ ppm; 0.82–0.97(m,6H), 1.08–2.16(m,15H), 2.30–2.63(m,3H), 2.71–3.02(m,2H), 2.90(d,J=5.4 Hz,1H), 3.17–3.64(m,5H), 3.76(s,3H), 4.08(s, 2H), 4.10–4.26(m,2H), 4.37–4.49(m,1H)

IR(neat) cm$^{-1}$: 3368,2930,2871,2236,1746,1456,1440, 1402,1380,1288,1214,1138, 1034,996,705

EXAMPLE 40

(11R,17R)-3-oxa-11-deoxy-11-(2-hydroxyethylsulfonyl)-17,20-dimethyl-13,14-didehydro-PGE$_1$ Methyl Etster(Compound 77)

To a chloroform solution (3 ml) of (11R,17R)-3-oxa-11-deoxy-11-(2-hydroxyethylthio)-17,20-dimethyl-13,14-didehydro-PGE$_1$ methyl ester obtained in Example 12 (40 mg) was added m-chloroperbenzoic acid (45 mg) at room temperature, followed by stirring at the same temperature for 30 minutes. The reaction solution was added to a mixture of ethyl acetate and a saturated aqueous sodium bicarbonate solution and, after separation of the organic layer, the aqueous layer was extracted with ethyl acetate, and the organic layers were combined, washed with a saturated aqueous sodium chloride solution and dried over anhydrous magnesium sulfate. Filtration and concentration gave a crude product, which was then purified by a silica gel column chromatography (developing solvent; hexane:ethyl acetate=1:2) to give the title compound (33 mg).

$^1$H-NMR(CDCl$_3$,300 MHz) δ ppm; 0.85–0.99(m,6H), 1.10–1.96(m,15H), 2.39–2.51(m,1H), 2.66–2.94(m,4H), 3.06–3.17(m,1H), 3.35(ddd,J=14.9,5.5,4.3 Hz,1H), 3.45–3.65(m,2H), 3.76(s,3H), 3.81(ddd,J=14,9,7.8,4.7 Hz,1H), 3.92–4.05(m,1H),4.08(s,2H), 4.10–4.28(m,2H), 4.40–4.53(m,1H)

IR(neat) cm$^{-1}$: 3470,2956,2930,2870,2236,1752,1746, 1456,1440,1402,1380,1321, 1284,1224,1127,1062,708,526

EXAMPLE 41

(2E,11R,17R)-11-deoxy-11-(2-hydroxyethylthio)-17-methyl-2,3,13,14-tetradehydro-PGE$_1$ Methyl Ester (Compound 52) and (2E,11S,17R)-11-deoxy-11-(2-hydroxyethylthio)-17-methyl-2,3,13,14-tetradehydro-PGE$_1$ Methyl Ester (Compound 53)

(1) Following the substantially same manner as in Example 1(1) using (2E,17R)-17-methyl-2,3,13,14-tetradehydro-PGE$_1$ methyl ester in place of (17R)-17,20-dimethyl-13,14-didehydro-PGE$_1$ methyl ester in Example 1(1), thereby (2E,17R)-17-methyl-2,3,13,14-tetradehydro-PGA$_1$ methyl ester was obtained.

$^1$H-NMR(CDCl$_3$,200 MHz) δ ppm; 0.76–2.50(m,20H), 0.92(d,J=6.6 Hz,3H), 3.34–3.52(m,1H), 3.74(s,3H), 4.29–4.57(m,1H), 5.85(dt,J=15.7,1.5 Hz,1H), 6.19(dd,J= 5.7,2.4 Hz,1H), 6.99(dt,J=15.7,7.0 Hz,1H), 7.48(dd,J=5.7, 2.4 Hz,1H)

IR(neat) cm$^{-1}$: 3436,2954,2930,2871,2214,1718,1654, 1594,1546,1460,1437,1381, 1274,1201,1178,1044,983,871

(2) Following the substantially same manner as in Example 1(2) using the compound obtained in the above (1), thereby the title compounds were obtained. (2E,11R,17R)-11-deoxy-11-(2-hydroxyethylthio)-17-methyl-2,3,13,14-tetradehydro-PGE$_1$ Methyl Ester $^1$H-NMR(CDCl$_3$,200 MHz) δ ppm; 0.81–1.00(m,3H), 0.93(d,J=6.6 Hz,3H), 1.07–1.90(m,13H), 2.00–3.00(m,7H), 2.11(dd,J=18.8,11.7 Hz,1H), 2.88(dt,J=14.1,6.4 Hz,1H), 3.14(dt,J=14.1,6.4 Hz,1H), 3.27(ddd,J=11.7,10.4,7.9 Hz,1H), 3.74(s,3H), 3.86(t,J=6.4 Hz,2H), 4.45(ddd,J=8.1, 5.8,1.9 Hz,1H), 5.83(dt,J=15.6,1.5 Hz,1H), 6.97(dt,J=15.6, 7.0 Hz,1H)

IR(neat) cm$^{-1}$: 3400,2930,2871,2230,1746,1724,1654, 1460,1438,1384,1314,1278, 1202,1175,1045,984,720

(2E,11S,17R)-11-deoxy-11-(2-hydroxyethylthio)-17-methyl-2,3,13,14-tetradehydro-PGE$_1$ Methyl Ester $^1$H-NMR(CDCl$_3$,200 MHz) δ ppm; 0.78–1.00(m,3H), 0.93(d,J=6.6 Hz,3H), 1.04–1.88(m,13H), 2.12–3.16(m, 10H), 3.57–3.68(m,1H), 3.73(s,3H), 3.87(dt,J=1.8,5.9 Hz,2H), 4.41–4.55(m,1H), 5.83(dt,J=15.7,1.5 Hz,1H), 6.97 (dt,J=15.7,7.0 Hz,1H)

IR(neat) cm$^{-1}$: 3400,2930,2871,2230,1740,1734,1654, 1460,1437,1402,1384,1278, 1202,1163,1046,984,740

EXAMPLE 42

(2E,11R,17R)-11-deoxy-11-(2-hydroxyethylthio)-17-methyl-2,3,13,14-tetradehydro-PGE$_1$ (Compound 54)

Following the substantially same manner as in Example 2 using (2E,11R,17R)-11-deoxy-11-(2-hydroxyethylthio)-17-methyl-2,3,13,14-tetradehydro-PGE$_1$ methyl ester obtained in Example 41, thereby the title compound was obtained.

$^1$H-NMR(CDCl$_3$,200 MHz) δ ppm; 0.81–1.02(m,3H), 0.93(d,J=6.6 Hz,3H), 1.06–3.42(m,24H), 2.11(dd,J=18.8, 11.8 Hz,1H), 3.87(t,J=6.4 Hz,2H), 4.46(ddd,J=10.9,5.9,1.8 Hz,1H), 5.85(dt,J=15.7,1.5 Hz,1H), 7.06(dt,J=15.7,7.0 Hz,1H)

IR(neat) cm$^{-1}$: 3368,2930,2871,2236,1740,1697,1654, 1460,1402,1383,1347,1283, 1228,1158,1048,1016,985,876, 740,670

EXAMPLE 43

(2E,11R)-11-deoxy-11-(2-hydroxyethylthio)-19,20dinor-17-methyl-2,3,13,14-tetradehydro-PGE$_1$ Methyl Ester (Compound 55) and (2E,11S)-11-deoxy-11-(2-hydroxyethylthio)-19,20-dinor-17-methyl-2,3,13,14-tetradehydro-PGE$_1$ Methyl Ester (Compound 56)

(1) Following the substantially same manner as in Example 1(1) using 19,20-dinor-17-methyl-2,3,13,14-tetradehydro-PGE$_1$ methyl ester in place of (17R)-17,20-dimethyl-13,14-didehydro-PGE$_1$ methyl ester in Example 1(1), thereby (2E)-19,20-dinor-17-methyl-2,3,13,14-tetradehydro-PGA$_1$ methyl ester was obtained.

$^1$H-NMR(CDCl$_3$,200 MHz) δ ppm; 0.93(d,J=6.6 Hz,3H), 0.94(d,J=6.4 Hz,3H),1.20–2.50(m,13H), 3.35–3.49(m,1H), 3.74(s,3H), 4.26–4.55(m,1H), 5.85(dt,J=15.7,1.5 Hz,1H), 6.19(dd,J=5.7,2.4 Hz,1H), 6.98(dt,J=15.7,6.9 Hz,1H), 7.48 (dd,J=5.7,2.4 Hz,1H IR(neat) cm$^{-1}$: 3436,2953,2868,2214,1718,1654,1594, 1541,1466,1437,1386,1368, 1274,1202,1176,1114,1039, 983,860,720

(2) Following the substantially same manner as in Example 1(2) using the compound obtained in the above (1), thereby the title compounds were obtained.

(2E,11R)-11-deoxy-11-(2-hydroxyethylthio)-19,20-dinor-17-methyl-2,3,13,14-tetradehydro-PGE$_1$ methyl ester $^1$H-NMR(CDCl$_3$,200 MHz) δ ppm; 0.94(d,J=6.6 Hz,3H), 0.96(d,J=6.6 Hz,3H), 1.18–1.96(m,10H), 2.02–2.36(m,4H), 2.12(dd,J=18.8,11.7 Hz,1H), 2.58–2.97(m,1H), 2.66(ddd,J= 11.7,10.5,1.9 Hz,1H), 2.88(dt,J=13.9,6.4 Hz,1H), 3.14(dt,J= 13.9,6.4 Hz,1H), 3.27(ddd,J=11.7,10.5,7.9 Hz,1H), 3.74(s, 3H), 3.86(t,J=6.4 Hz,2H), 4.44(dt,J=1.9,7.3 Hz,1H), 5.84(dt, J=15.7,1.5 Hz,1H), 6.97(dt,J=15.7,6.9 Hz,1H)

IR(neat) cm$^{-1}$: 3427,2930,2869,2236,1734,1654,1462, 1456,1436,1402,1368,1278, 1202,1174,1045,986,924,844, 720,536

(2E,11S)-11-deoxy-11-(2-hydroxyethylthio)-19,20-dinor-17-methyl-2,3,13,14-tetradehydro-PGE$_1$ Methyl Ester $^1$H-NMR(CDCl$_3$,200 MHz) δ ppm; 0.94(d,J=6.6 Hz,3H), 0.96(d,J=6.6 Hz,3H), 1.19–2.01(m,10H), 2.11–3.15(m,9H), 3.57–3.68(m,1H), 3.73(s,3H), 3.81(dt,J=1.7,6.0 Hz,2H), 4.47(dt,J=1.8,7.3 Hz,1H), 5.83(dt,J=15.6,1.5 Hz,1H), 6.97 (dt,J=15.6,7.0 Hz,1H)

IR(neat) cm$^{-1}$: 3400,2930,2867,2230,1734,1654,1466, 1437,1402,1385,1368,1278, 1202,1164,1045,844,720

EXAMPLE 44

(2E,11R)-11-deoxy-11-(2-hydroxyethylthio)-19,20-dinor-17-methyl-2,3,13,14-tetradehydro-PGE$_1$ (Compound 57)

Following the substantially same manner as in Example 2 using (2E, 11R,17R)-11-deoxy-11-(2-hydroxyethylthio)-19, 20-dinor-17-methyl-2,3,13,14-tetradehydro-PGE$_1$ methyl ester obtained in Example 43, thereby the title compound was obtained.

$^1$H-NMR(CDCl$_3$,200 MHz) δ ppm; 0.94(d,J=6.6 Hz,3H), 0.96(d,J=6.4 Hz,3H), 1.34–1.96(m,9H), 2.01–3.38(m,8H), 2.11(dd,J=18.9,11.7 Hz,1H), 2.87(dt,J=14.0,6.4 Hz,1H), 3.15(dt,J=14.0,6.4 Hz,1H), 3.28(ddd,J=11.7,10.5,7.9 Hz,1H), 3.86(t,J=6.4 Hz,2H), 4.44(dt,J=1.8,7.3 Hz,1H), 5.84(dt,J=15.6,1.4 Hz,1H), 7.06(dt,J=15.6,7.0 Hz,1H)

IR(neat) cm$^{-1}$: 3368,2930,2869,2236,1740,1697,1654, 1466,1402,1368,1284,1218, 1163,1046,985,670,539

EXAMPLE 45

(2E,11R,17R)-11-deoxy-11-(2-hydroxyethylthio)-20-hydroxy-17-methyl-2,3,13,14-tetradehydro-PGE$_1$ Methyl Ester (Compound 119) and (2E,11S,17R)-11-deoxy-11-(2-hydroxyethylthio)-20-hydroxy-17-methyl-2,3,13,14-tetradehydro-PGE$_1$ methyl ester (Compound 121)

(1) Following the substantially same manner as in Example 1(1) using (2E,17R)-20-hydroxy-17-methyl-2,3, 13,14-tetradehydro-PGE$_1$ methyl ester in place of (17R)-17, 20-dimethyl-13,14-didehydro-PGE$_1$ methyl ester in Example 1(1), thereby (2E,17R)-20-hydroxy-17-methyl-2, 3,13,14-tetradehydro-PGA$_1$ methyl ester was obtained.

$^1$H-NMR(CDCl$_3$,300 MHz) δ ppm; 0.92–0.98(m,3H), 1.15–1.98(m,15H), 2.14–2.45(m,3H), 3.39–3.45(m,1H), 3.64(t,J=6.6 Hz,2H), 3.74(s,3H), 4.40–4.52(m,1H), 5.85(d, J=15.7 Hz,1H), 6.19(dd,J=5.8,2.3 Hz,1H), 6.98(dt,J=15.7, 7.0 Hz,1H), 7.47(dd,J=5.8,2.5 Hz,1H)

IR(neat) cm$^{-1}$: 3400,2934,2860,2214,1708,1702,1654, 1437,1384,1277,1202,1179, 1055,876,719

(2) Following the substantially same manner as in Example 1(2) using the compound obtained in the above (1), thereby the title compounds were obtained.

(2E,11R,17R)-11-deoxy-11-(2-hydroxyethylthio)-20-hydroxy-17-methyl-2,3,13,14-tetradehydro-PGE$_1$ Methyl Ester $^1$H-NMR(CDCl$_3$, 300 MHz) δ ppm; 0.88–1.00(m,3H), 1.16–2.34(m,19H), 2.12(dd,J=18.9,11.7 Hz,1H), 2.60–2.97 (m,3H), 3.13(dt,J=13.6,6.8 Hz,1H), 3.21–3.34(m,1H), 3.59–3.70(m,2H), 3.73(s,3H), 3.77–3.89(m,2H), 4.40–4.52 (m,1H), 5.79–5.89(m,1H), 6.90–7.04(m,1H)

IR(neat) cm$^{-1}$: 3400,2930,2860,2236,1740,1724,1654, 1438,1402,1384,1283,1203, 1176,1046,720

(2E,11S,17R)-11-deoxy-11-(2-hydroxyethylthio)-20-hydroxy-17-methyl-2,3,13,14-tetradehydro-PGE$_1$ Methyl Ester $^1$H-NMR(CDCl$_3$,300 MHz) δ ppm; 0.89–1.01(m,3H), 1.35–1.86(m,13H), 2.15–2.29(m,4H), 2.47–2.66(m,4H), 2.87–3.13(m,3H), 3.58–3.88(m,5H), 3.73(s,3H), 4.44–4.54 (m,1H), 5.83(dt,J=15.6,1.5 Hz,1H), 6.96(dt,J=15.6,7.1 Hz,1H)

IR(neat) cm$^{-1}$ : 3400,2934,2864,2230,1740,1724,1654, 1437,1402,1380,1284,1202, 1177,1050,720

EXAMPLE 46

(2E,11R,17R)-11-deoxy-11-(2-hydroxyethylthio)-20-methoxy-17-methyl-2,3,13,14-tetradehydro-PGE$_1$ Methyl Ester (Compound 124) and (2E,11S,17R)-11-deoxy-11-(2-hydroxyethylthio)-20-methoxy-17-methyl-2,3,13,14-tetradehydro-PGE$_1$ Methyl Ester (Compound 126)

(1) Following the substantially same manner as in Example 1(1) using (2E,17R)-20-methoxy-17-methyl-2,3,13,14-tetradehydro-PGE$_1$ methyl ester in place of (17R)-17,20-dimethyl-13,14-didehydro-PGE$_1$ methyl ester in Example 1(1), thereby (2E,17R)-20-methoxy-17-methyl-2,3,13,14-tetradehydro-PGA$_1$ methyl ester was obtained.

$^1$H-NMR(CDCl$_3$,300 MHz) δ ppm; 0.90–0.98(m,3H), 1.14–2.46(m,18H), 3.30–3.45(m,2H), 3.33(s,3H), 3.73(s,3H), 4.39–4.52(m,1H), 5.84(dt,J=15.7,1.6 Hz,1H), 6.19(dd,J=5.6,2.3 Hz,1H), 6.98(dt,J=15.7,7.1 Hz,1H), 7.47(dd,J=5.6,2.3 Hz,1H)

IR(neat) cm$^{-1}$: 3436,2930,2860,2214,1718,1702,1654, 1437,1384,1273,1201,1116, 1039,984,670

(2) Following the substantially same manner as in Example 1(2) using the compound obtained in the above (1), thereby the title compounds were obtained.

(2E,11R,17R)-11-deoxy-11-(2-hydroxyethylthio)-20-methoxy-17-methyl-2,3,13,14-tetradehydro-PGE$_1$ Methyl Ester $^1$H-NMR(CDCl$_3$,300 MHz) δ ppm; 0.89–0.99(m,3H), 1.15–1.85(m,15H), 2.11(dd,J=19.0,11.7 Hz,1H), 2.14–2.33(m,3H), 2.60–2.93(m,3H), 3.13(dt,J=13.7,6.8 Hz,1H), 3.20–3.41(m,3H), 3.33(s,3H), 3.73(s,3H), 3.78–3.89(m,2H), 4.39–4.50(m,1H), 5.83(d,J=15.5 Hz,1H), 6.96(dt,J=15.5,7.0 Hz,1H)

IR(neat) cm$^{-1}$: 3420,2930,2860,2236,1745,1724,1654, 1456,1436,1402,1278,1202, 1116,1045,848,720,595

(2E,11S,17R)-11-deoxy-11-(2-hydroxyethylthio)-20-methoxy-17-methyl-2,3,13,14-tetradehydro-PGE$_1$ Methyl Ester $^1$H-NMR(CDCl$_3$,300 MHz) δ ppm; 0.95(d,J=6.4 Hz,3H), 1.13–1.84(m,13H), 2.16–2.28(m,3H), 2.46–2.67(m,4H), 2.86–3.13(m,3H), 3.30–3.41(m,2H), 3.33(s,3H), 3.58–3.66(m,1H), 3.71–3.86(m,2H), 3.73(s,3H), 4.44–4.53(m,1H), 5.83(dt,J=15.6,1.6 Hz,1H), 6.96(dt,J=15.6,7.0 Hz,1H)

IR(neat) cm$^{-1}$: 3427,2930,2860,2236,1740,1724,1654, 1437,1401,1278,1202,1178, 1116,1045,720

EXAMPLE 47

(2E,11R,17R)-11-deoxy-11-(2-hydroxyethylthio)-20-methoxy-17-methyl-2,3,13,14-tetradehydro-PGE$_1$ (Compound 128)

Following the substantially same manner as in Example 2 using (2E,11R,17R)-11-deoxy-11-(2-hydroxyethylthio)-20-methoxy-17-methyl-2,3,13,14-tetradehydro-PGE$_1$ methyl ester in Example 46, thereby the title compound was obtained.

$^1$H-NMR(CDCl$_3$,300 MHz) δ ppm; 0.91–0.98(m,3H), 1.16–1.86(m,16H), 2.11(dd,J=18.9,11.9 Hz,1H), 2.24–2.34(m,3H), 2.59–2.93(m,3H), 3.07–3.51(m,4H), 3.37(s,3H), 3.85(t,J=6.5 Hz,2H), 4.40–4.50(m,1H), 5.84(d,J=15.6 Hz,1H), 7.01(dt,J=15.6,7.2 Hz,1H)

IR(neat) cm$^{-1}$: 3394,2930,2860,2236,1745,1697,1654, 1461,1402,1283,1206,1157, 1114,1046,986,876,666

Experiment

Determination of DNA synthesis inhibition activity of PGE$_1$ derivatives to human vascular smooth muscle cells On a plate with 24 wells (manufactured by Corning Co.), 1×10$^4$ cells/well of quintic culture cells of vascular cells derived from normal human aorta (manufactured by Kurabo Co.) were inoculated and cultured for 2 days. The medium was exchanged from the growth medium (SG2: manufactured by Kurabo Co.) to the basal medium (SB2: manufactured by Kurabo Co.), and cultured for 24 hours, to which was added the growth medium (SG2) containing an ethanol solution of the test compound. 0.01 mci/well of $^3$H-thymidine (manufactured by Daiichi Chemicals Co.) was added and, after culturing for 24 hours, the cultured supernatant was removed by suction, followed by washing with a phosphate buffer solution (PBS).

5% Trichloroacetic acid (TCA) was added and, after allowing to stand at 4° C. for 20 minutes, the mixture was washed once with TCA. The mixture was washed with PBS, and dissolved in 0.5 M aqueous potassium hydroxide solution. Intake of $^3$H-thymidine was determined using 20 μl of the aqueous potassium hydroxide solution dissolving the cells which incorporated $^3$H-thymidine in the nucleus by means of a liquid scintillation counter (manufactured by Hewlett-Packard Co.).

Results are shown in Table 1.

TABLE 1

| Test compound | Growth inhibition rate (percent to control) |
| --- | --- |
| Compound 7 | 98.4 |
| Compound 70 | 95.6 |
| Compound 92 | 99.3 |

Note: Compounds 7, 70 and 92 in the table are those which were prepared in Examples. The test compounds were each used as an ethanol solution (the concentration of the added compound: 1×10$^{-5}$ M), and compared with control (vehicle-treated group).

As a result, Compounds 7, 70 and 92 were found to have a high growth inhibition activity against human vascular smooth muscle cells.

Industrial Applicability

The present invention makes it possible to provide PG derivatives which exhibit excellent action in inhibiting the growth of vascular smooth muscle cells and are useful as a drug for inhibition of vascular thickening (e.g. a cause of restenosis after percutaneous transluminal coronary angioplasty) and vascular occlusion, or useful as a drug for prevention or therapy of vascular thickening and vascular occlusion.

What is claimed is:

1. A prostaglandin derivative represented by the formula:

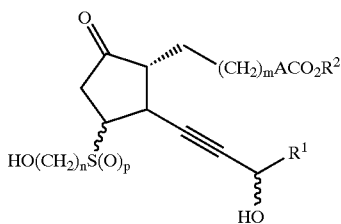

(I)

wherein A is an ethylene group, a vinylene group, an ethynylene group, O(CH₂)q or S(O)r(CH₂)q, $R^1$ is a $C_{3-10}$ cycloalkyl group, a $C_{1-4}$ alkyl-$C_{3-10}$ cycloalkyl group, a $C_{3-10}$ cycloalkyl-$C_{1-4}$ alkyl group, a $C_{1-10}$ cycloalkyl-$C_{1-4}$ alkyl group, a $C_{1-10}$ alkyl group, a $C_{1-10}$ alkyl group substituted with hydroxyl group(s) or $C_{1-4}$ alkoxy group(s), a $C_{2-10}$ alkenyl group, a $C_{2-10}$ alkenyl group substituted with hydroxyl group(s) or $C_{1-4}$ alkoxy group(s), a $C_{2-10}$ alkynyl group, a $C_{2-10}$ alkynyl group substituted with hydroxyl group(s) or $C_{1-4}$ alkoxy group(s) or a bridged cyclic hydrocarbon group, $R^2$ is a hydrogen atom, a $C_{1-10}$ alkyl group or a $C_{3-10}$ cycloalkyl group, m is an integer of 1 to 5, n is an integer of 1 to 4, p is 0, 1 or 2, q is an integer of 1 to 5 and r is 0, 1 or 2; a pharmaceutically acceptable salt thereof or a hydrate thereof.

2. The prostaglandin derivative according to claim 1 represented by Formula (I) wherein $R^1$ is a $C_{5-10}$ alkyl group, a $C_{5-10}$ alkyl group substituted with hydroxyl group(s) or $C_{1-4}$ alkoxy group(s), a $C_{5-10}$ alkenyl group, a $C_{5-10}$ alkenyl group substituted with hydroxyl group(s) or $C_{1-4}$ alkoxy group(s), a $C_{5-10}$ alkynyl group or a $C_{5-10}$ alkynyl group substituted with hydroxyl group(s) or $C_{1-4}$ alkoxy group(s), and q is 1 or 2, the pharmaceutically acceptable salt thereof or the hydrate thereof.

3. The prostaglandin derivative according to claim 1 represented by Formula (I) wherein m is an integer of 2 to 4, and n is 2 or 3, the pharmaceutically acceptable salt thereof or the hydrate thereof.

4. The prostaglandin derivative according to claim 1 represented by Formula (I) wherein p is 0, the pharmaceutically acceptable salt thereof or the hydrate thereof.

5. A pharmaceutical preparation which comprises as an effective ingredient the prostaglandin derivative according to claim 1, the pharmaceutically acceptable salt thereof or the hydrate thereof.

6. The pharmaceutical preparation according to claim 5, which is a pharmaceutical preparation for growth inhibition of vascular smooth muscle.

7. The pharmaceutical preparation according to claim 5, which is a pharmaceutical preparation for prevention or therapy of the restenosis after PTCA.

* * * * *

UNITED STATES PATENT AND TRADEMARK OFFICE
CERTIFICATE OF CORRECTION

PATENT NO. : 6,455,584 B1
DATED : October 3, 2002
INVENTOR(S) : Sato et al.

It is certified that error appears in the above-identified patent and that said Letters Patent is hereby corrected as shown below:

<u>Title page,</u>
Item [57], ABSTRACT,
Line 3, Formula
which reads: "

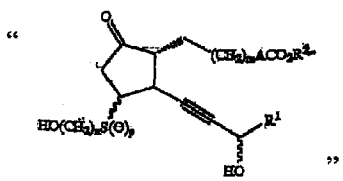

"

should read: --

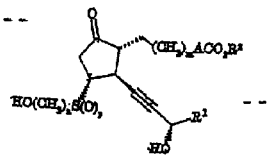

--

<u>Column 1,</u>
Lines 56 and 65, Formula
which reads: "

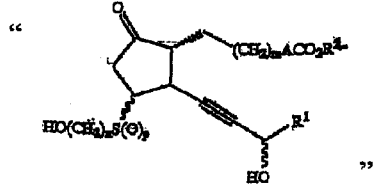

"

should read: --

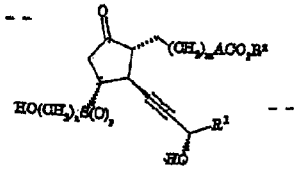

--

<u>Column 12,</u>
Line 42, "7.4 Hz," should read -- 7.4Hz --.

<u>Column 15,</u>
Line 36, "1379, 1345" should read -- 1379, 1345 --.

<u>Column 21,</u>
Line 33, "--13, 14" should read -- -13, 14 --.

UNITED STATES PATENT AND TRADEMARK OFFICE
CERTIFICATE OF CORRECTION

PATENT NO.    : 6,455,584 B1
DATED         : October 3, 2002
INVENTOR(S)   : Sato et al.

It is certified that error appears in the above-identified patent and that said Letters Patent is hereby corrected as shown below:

Column 25,
Line 66, "1285, 1211" should read -- 1285, 1211 --.

Column 27,
Line 66, "1384, 1345" should read -- 1384, 1345 --.

Column 31,
Line 23, "20dinor" should read -- 20-dinor --.

Column 35,
Lines 3-13, Formula
which reads:

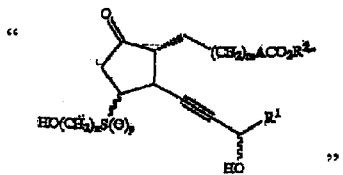

should read:

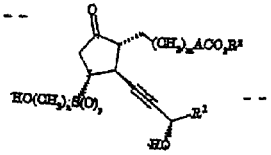

Signed and Sealed this

Seventeenth Day of December, 2002

JAMES E. ROGAN
*Director of the United States Patent and Trademark Office*

UNITED STATES PATENT AND TRADEMARK OFFICE
CERTIFICATE OF CORRECTION

PATENT NO. : 6,455,584 B1
DATED : September 24, 2002
INVENTOR(S) : Sato et al.

It is certified that error appears in the above-identified patent and that said Letters Patent is hereby corrected as shown below:

Title page,
Item [57], ABSTRACT,
Line 3, Formula which reads: "

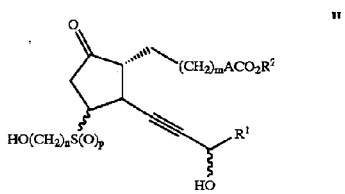

"

should read: --

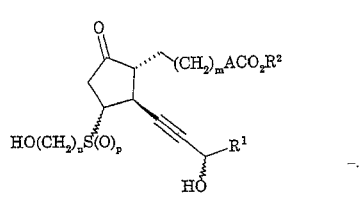

Column 1,
Lines 55 and 65, Formula which reads: "

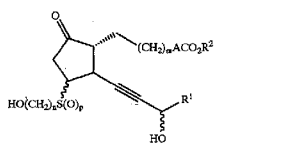

"

should read: "

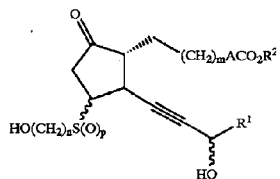

"

Column 2,
Line 42, "cyclobu-" should read -- a cyclobu- --.

Column 3,
The second formula in the left-hand column which reads:

"

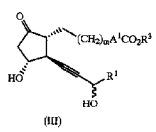

"

should read: --

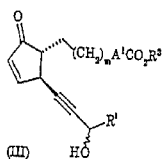

--.

UNITED STATES PATENT AND TRADEMARK OFFICE
CERTIFICATE OF CORRECTION

PATENT NO. : 6,455,584 B1
DATED : September 24, 2002
INVENTOR(S) : Sato et al.

It is certified that error appears in the above-identified patent and that said Letters Patent is hereby corrected as shown below:

Column 12,
Line 42, "1.12(t,J=7.4 Hz,3H)" should read -- 1.12(t,J=7.4Hz,3H) --.

Column 15,
Line 36, "1379, 1345" should read -- 1379,1345 --.

Column 19,
Line 26, "(11R,15R,17R)-3-oxa-11-deoxy-1-(2-" should read -- (11R,15R,17R)-3-oxa-11-deoxy-11-(2- --.

Column 21,
Line 33, "methy--13,14-" should read -- methyl-13,14- --; and
Line 53, "(CDC$_3$" should read -- (CDCl$_3$ --.

Column 22,
Line 55, "(11R,17R)-3-oxa-11-deoxy-1-(2-hydroxyethylthio)-" should read -- (11R,17R)-3-oxa-11-deoxy-11-(2-hydroxyethylthio)- --.

Column 25
Line 66, "1285, 1211" should read -- 1285,1211 --.

Column 27,
Line 66, "1384, 1345" should read -- 1384,1345 --.

Column 28,
Line 17, "2.-14 2.41" should read -- 2.31-2.41 --.

Column 29,
Line 12, "3.-14 3.85" should read -- 3.31-3.85 --.

Column 31,
Line 23, "20dinor" should read -- 20-dinor --.

Column 32,
Line 10, "(2E, 11R, 17R)" should read -- (2E,11R) --.

UNITED STATES PATENT AND TRADEMARK OFFICE
CERTIFICATE OF CORRECTION

PATENT NO.   : 6,455,584 B1
DATED        : September 24, 2002
INVENTOR(S)  : Sato et al.

It is certified that error appears in the above-identified patent and that said Letters Patent is hereby corrected as shown below:

Column 35,
The formula at line 2 which reads:

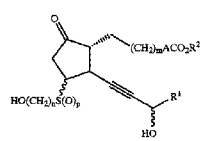

should read:

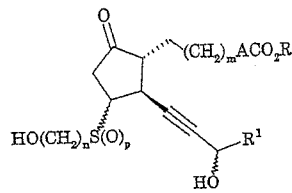

Line 17, delete "cycloalkyl-$C_{1-4}$"; and
Line 18, delete "alkyl group, a $C_{1-10}$".

This certificate supersedes Certificate of Correction issued December 17, 2002.

Signed and Sealed this

Twenty-fifth Day of March, 2003

JAMES E. ROGAN
*Director of the United States Patent and Trademark Office*